US012721870B2

(12) United States Patent
Kang et al.

(10) Patent No.: US 12,721,870 B2
(45) Date of Patent: Sep. 1, 2026

(54) ***LACTOBACILLUS FERMENTUM* ATG-V5 STRAIN, OR COMPOSITION FOR ENHANCING IMMUNITY COMPRISING SAME**

(71) Applicants: ATOGEN CO., LTD, Daejeon (KR); M. S. BIOTECH CO., LTD, Chungcheongbuk-do (KR); Ji Hee Kang, Daejeon (KR)

(72) Inventors: Ji Hee Kang, Daejeon (KR); Yeon Hwa Park, Siheung-si (KR); Dong Kwan Ju, Yongin-si (KR); Yo Han Ju, Hwaseong-si (KR); Ye Won Kang, Daejeon (KR); Gun Seok Park, Daejeon (KR); Seung Hyun Ko, Daejeon (KR)

(73) Assignees: ATOGEN CO., LTD, Daejeon (KR); M. S. BIOTECH CO., LTD, Eumseong-gun (KR); Ji Hee Kang, Daejeon (KR)

( * ) Notice: Subject to any disclaimer, the term of this patent is extended or adjusted under 35 U.S.C. 154(b) by 333 days.

(21) Appl. No.: 18/288,640

(22) PCT Filed: Apr. 14, 2022

(86) PCT No.: PCT/KR2022/005413
§ 371 (c)(1),
(2) Date: Oct. 27, 2023

(87) PCT Pub. No.: WO2022/231178
PCT Pub. Date: Nov. 3, 2022

(65) Prior Publication Data

US 2024/0207333 A1 Jun. 27, 2024

(30) Foreign Application Priority Data

Apr. 27, 2021 (KR) ........................ 10-2021-0054315

(51) Int. Cl.

| | |
|---|---|
| ***A61K 35/747*** | (2015.01) |
| ***A61P 1/14*** | (2006.01) |
| ***A61P 37/04*** | (2006.01) |
| ***C12N 1/205*** | (2026.01) |
| ***C12R 1/225*** | (2006.01) |

(52) U.S. Cl.
CPC .............. *A61K 35/747* (2013.01); *A61P 1/14* (2018.01); *A61P 37/04* (2018.01); *C12N 1/205* (2021.05); *C12R 2001/225* (2021.05)

(58) Field of Classification Search
CPC .......... A61K 35/747; A61P 1/14; A61P 37/04; A61P 37/00; C12N 1/205; C12N 1/20; C12R 2001/225; A23L 33/135; A23V 2002/00; A23V 2200/324
See application file for complete search history.

(56) References Cited

FOREIGN PATENT DOCUMENTS

| | | | |
|---|---|---|---|
| EP | 2 520 644 | A1 | 11/2012 |
| KR | 10-1488770 | B1 | 2/2015 |
| KR | 10-1511976 | B1 | 4/2015 |
| KR | 10-1862051 | B1 | 5/2018 |
| KR | 10-1980527 | B1 | 5/2019 |
| KR | 10-2106737 | B1 | 5/2020 |
| WO | 2019/103198 | A1 | 5/2019 |

OTHER PUBLICATIONS

Garcia-Castillo et al., "Evaluation of the Immunomodulatory Activities of the Probiotic Strain Lactobacillus fermentum UCO-979C", Jun. 13, 2019, Frontiers in Immunology, vol. 10 Article 1376, whole document (Year: 2019).*

Perez-Cano et al., "In vitro immunomodulatory activity of Lactobacillus fermentum CECT5716 and Lactobacillus salivarius CECT5713: two probiotic strains isolated from human breast milk" Jan. 29, 2010, Immunobiology 215, 996-1004 (Year: 2010).*

Heppner GH, Miller BE. Tumor heterogeneity: biological implications and therapeutic consequences. Cancer Metastasis Rev. 1983; 2(1):5-23. doi: 10.1007/BF00046903. PMID: 6616442. (Year: 1983).*

Abedin-Do A, Taherian-Esfahani Z, Ghafouri-Fard S, Ghafouri-Fard S, Motevaseli E. Immunomodulatory effects of Lactobacillus strains: emphasis on their effects on cancer cells. Immunotherapy. 2015;7(12):1307-29. doi: 10.2217/imt.15.92. Epub Nov. 23, 2015. PMID: 26595390. (Year: 2015).*

Marinelli L, Tenore GC, Novellino E. Probiotic species in the modulation of the anticancer immune response. Semin Cancer Biol. Oct. 2017;46:182-190. doi: 10.1016/j.semcancer.2017.08.007. Epub Aug. 24, 2017. PMID: 28844794. (Year: 2017).*

International Search Report for PCT/KR2022/005413 dated Jul. 15, 2022.

Valeria Garcia-Castillo, et al.,"Evaluation of the immunomdulatory Activities of the Probiotic Stain Lactobacillus Fermentum UCO-979C", Frontiers in Immunology, Jun. 2019, vol. 10, Article 1376, (14 pages).

(Continued)

*Primary Examiner* — Anne M. Gussow
*Assistant Examiner* — Amelia Stephens
(74) *Attorney, Agent, or Firm* — Sughrue Mion, PLLC

(57) ABSTRACT

The present invention relates to a novel *lactobacillus fermentum* ATG-V5 strain or a composition for enhancing immunity, comprising same. The *Lactobacillus fermentum* ATG-V5 strain of the present invention has no cytotoxicity, and has the effect of enhancing immunity, such as increasing the amounts of nitric oxide (NO), interleukin 6 (IL-6) and tumor necrosis factor (TNF) secretion and phagocytosis of macrophages, reducing the amount of interleukin 1β (IL-1β) secretion of macrophages, increasing the cell viability of splenocytes, and increasing the amount of antibodies and cytokines secretion in the blood, and thus the strain can be effectively used as a material for a composition and a health functional food for enhancing immunity, and the composition and health functional food can be effectively used in enhancing individual immune activity. In addition, a health functional food comprising the food composition is also effective in enhancing individual immune activity.

9 Claims, 30 Drawing Sheets

Specification includes a Sequence Listing.

(56) References Cited

OTHER PUBLICATIONS

Extended European Search Report dated Oct. 9, 2024 in Application No. 22796012.7.

* cited by examiner

Fig. 1

1. 16s rRNA SEQUENCE OF *Lactobacillus fermentum* ATG-V5

ATGCAGTCGAACGCGTTGGCCCAATTGATTGATGGTGCTTGCACCTGATTGATTTTGGTCGCCAACGAGTGGC
GGACGGGTGAGTAACACGTAGGTAACCTGCCCAGAAGCGGGGGACAACATTTGGAAACAGATGCTAATACC
GCATAACAGCGTTGTTCGCATGAACAACGCTTAAAAGATGGCTTCTCGCTATCACTTCTGGATGGACCTGCGG
TGCATTAGCTTGTTGGTGGGGTAACGGCCTACCAAGGCGATGATGCATAGCCGAGTTGAGAGACTGATCGGC
CACAATGGGACTGAGACACGGCCCATACTCCTACGGGAGGCAGCAGTAGGGAATCTTCCACAATGGGCGCA
AGCCTGATGGAGCAACACCGCGTGAGTGAAGAAGGGTTTCGGCTCGTAAAGCTCTGTTGTTAAAGAAGAACA
CGTATGAGAGTAACTGTTCATACGTTGACGGTATTTAACCAGAAAGTCACGGCTAACTACGTGCCAGCAGCCG
CGGTAATACGTAGGTGGCAAGCGTTATCCGGATTTATTGGGCGTAAAGAGAGTGCAGGCGGTTTTCTAAGTCT
GATGTGAAAGCCTTCGGCTTAACCGGAGAAGTGCATCGGAAACTGGATAACTTGAGTGCAGAAGAGGGTAGT
GGAACTCCATGTGTAGCGGTGGAATGCGTAGATATATGGAAGAACACCAGTGGCGAAGGCGGCTACCTGGTC
TGCAACTGACGCTGAGACTCGAAAGCATGGGTAGCGAACAGGATTAGATACCCTGGTAGTCCATGCCGTAAA
CGATGAGTGCTAGGTGTTGGAGGGTTTCCGCCCTTCAGTGCCGGAGCTAACGCATTAAGCACTCCGCCTGGG
GAGTACGACCGCAAGGTTGAAACTCAAAGGAATTGACGGGGGCCCGCACAAGCGGTGGAGCATGTGGTTTA
ATTCGAAGCTACGCGAAGAACCTTACCAGGTCTTGACATCTTGCGCCAACCCTAGAGATAGGGCGTTTCCTTC
GGGAACGCAATGACAGGTGGTGCATGGTCGTCGTCAGCTCGTGTCGTGAGATGTTGGGTTAAGTCCCGCAAC
GAGCGCAACCCTTGTTACTAGTTGCCAGCATTAAGTTGGGCACTCTAGTGAGACTGCCGGTGACAAACCGGA
GGAAGGTGGGGACGACGTCAGATCATCATGCCCCTTATGACCTGGGCTACACACGTGCTACAATGGACGGTA
CAACGAGTCGCGAACTCGCGAGGGCAAGCAAATCTCTTAAAACCGTTCTCAGTTCGGACTGCAGGCTGCAAC
TCGCCTGCACGAAGTCGGAATCGCTAGTAATCGCGGATCAGCATGCCGCGGTGAATACGTTCCCGGGCCTTGT
ACACACCGCCCGTCACACCATGAGAGTTTGTAACACCCAAAGTCGGTGGGGTAACCTTTTAGGAGCCAGCCG
CCTAA

Fig. 3

| | Histidine | Lysine | Tyrosine | Ornithine |
|---|---|---|---|---|
| Positive control | | | | |
| V5 | | | | |
| Positive control: Escherichia coli KCTC1682 | | | | |

Fig. 14e

SEQUENCE LISTING

```
<160> NUMBER OF SEQ ID NOS: 1

<210> SEQ ID NO 1
<211> LENGTH: 1448
<212> TYPE: DNA
<213> ORGANISM: Artificial Sequence
<220> FEATURE:
<223> OTHER INFORMATION: 16S rRNA of Limosilactobacillus fermentum
      ATG-V5

<400> SEQUENCE: 1

atgcagtcga acgcgttggc ccaattgatt gatggtgctt gcacctgatt gattttggtc     60

gccaacgagt ggcggacggg tgagtaacac gtaggtaacc tgcccagaag cgggggacaa    120

catttggaaa cagatgctaa taccgcataa cagcgttgtt cgcatgaaca acgcttaaaa    180

gatggcttct cgctatcact tctggatgga cctgcggtgc attagcttgt tggtggggta    240

acggcctacc aaggcgatga tgcatagccg agttgagaga ctgatcggcc acaatgggac    300

tgagacacgg cccatactcc tacgggaggc agcagtaggg aatcttccac aatgggcgca    360

agcctgatgg agcaacaccg cgtgagtgaa gaagggtttc ggctcgtaaa gctctgttgt    420

taaagaagaa cacgtatgag agtaactgtt catacgttga cggtatttaa ccagaaagtc    480

acggctaact acgtgccagc agccgcggta atacgtaggt ggcaagcgtt atccggattt    540

attgggcgta aagagagtgc aggcggtttt ctaagtctga tgtgaaagcc ttcggcttaa    600
```

-continued

```
ccggagaagt gcatcggaaa ctggataact tgagtgcaga agagggtagt ggaactccat    660
gtgtagcggt ggaatgcgta gatatatgga agaacaccag tggcgaaggc ggctacctgg    720
tctgcaactg acgctgagac tcgaaagcat gggtagcgaa caggattaga taccctggta    780
gtccatgccg taaacgatga gtgctaggtg ttggagggtt tccgcccttc agtgccggag    840
ctaacgcatt aagcactccg cctggggagt acgaccgcaa ggttgaaact caaaggaatt    900
gacgggggcc cgcacaagcg gtggagcatg tggtttaatt cgaagctacg cgaagaacct    960
taccaggtct tgacatcttg cgccaaccct agagataggg cgtttccttc gggaacgcaa   1020
tgacaggtgg tgcatggtcg tcgtcagctc gtgtcgtgag atgttgggtt aagtcccgca   1080
acgagcgcaa cccttgttac tagttgccag cattaagttg ggcactctag tgagactgcc   1140
ggtgacaaac cggaggaagg tggggacgac gtcagatcat catgcccctt atgacctggg   1200
ctacacacgt gctacaatgg acggtacaac gagtcgcgaa ctcgcgaggg caagcaaatc   1260
tcttaaaacc gttctcagtt cggactgcag gctgcaactc gcctgcacga agtcggaatc   1320
gctagtaatc gcggatcagc atgccgcggt gaatacgttc ccgggccttg tacacaccgc   1380
ccgtcacacc atgagagttt gtaacaccca aagtcggtgg ggtaaccttt taggagccag   1440
ccgcctaa                                                            1448
```

*LACTOBACILLUS FERMENTUM* ATG-V5 STRAIN, OR COMPOSITION FOR ENHANCING IMMUNITY COMPRISING SAME

CROSS REFERENCE TO RELATED APPLICATIONS

This application is a National Stage of International Application No. PCT/KR2022/005413 filed Apr. 14, 2022, claiming priority based on Korean Patent Application No. 10-2021-0054315 filed Apr. 27, 2021, the entire disclosures of which are incorporated herein by reference.

INCORPORATION BY REFERENCE OF SEQUENCE LISTING

The content of the electronically submitted sequence listing, file name: Q292817_sequence listing as filed.txt; size: 2,441 bytes; and date of creation: Oct. 25, 2023, filed herewith, is incorporated herein by reference in its entirety.

TECHNICAL FIELD

The present disclosure relates to a novel *Lactobacillus fermentum* ATG-V5 strain or an immunity-enhancing composition containing the same.

BACKGROUND ART

Immunity refers to a state where upon generation of specific cells or other substances, such as microorganisms and tissues of the same species, that invade the human body from outside, the ability to produce antibodies is exhibited by recognizing the same as antigens with the involvement of the immune system and reacting specifically thereto to maintain homeostasis of individuals. Examples of cells involved in immune responses include lymphocytes, macrophages, natural killer cells (NK cells), dendritic cells, and the like. Recently, with the increasing attention to immunotherapies in which natural products are used for treatment rather than artificial compounds, many attempts have been made to explore naturally derived materials with the efficacy of enhancing immune activities.

Live microorganisms that provide health benefits to hosts by improving intestinal microbial environments within the gastrointestinal tracts of animals, including humans, are collectively referred to as probiotics. Excellent acid resistance, bile resistance, and adhesion ability to intestinal epithelial cells are practically required in most cases to exhibit effects as probiotics during oral intake. Lactic acid bacteria coexist in the human digestive system while serving to break down fibers and complex proteins into important nutrients and thus are used as probiotics. Lactic acid bacteria have been reported to exhibit the following effects: maintaining normal intestinal flora, improving intestinal flora, being antidiabetic and antihyperlipidemic, inhibiting carcinogenesis, inhibiting colitis, being nonspecifically active in the host's immune system, and the like. Among these, strains of the genus *Lactobacillus*, the main members of the normal microbial community residing in the human intestine, have long been known to be crucial in maintaining healthy digestive organs and a vaginal environment. In addition, according to the U.S. Public Health Service guidelines, all *Lactobacillus* strains currently deposited in the American Type Culture Collection (ATCC) are classified as "Biosafety Level 1" where no potential hazards to cause diseases in humans or animals are recognized to be known. On the other hand, kimchi lactic acid bacteria, lactic acid bacteria involved in kimchi fermentation, have been reported to have the following effects: enhancing immunity, being antimicrobial, antioxidant, anticancer, and antiobesity, preventing hypertension or constipation, and the like [Hivak P, Odrska J, Ferencik M, Ebringer L, Jahnova E, Mikes Z. : One-year application of Probiotic strain *Enterococcus* facium M-74 decreases Serum cholesterol levels. : Bratisl lek Listy 2005; $10^6$(2); 67-72; Agerholm-Larsen L. Bell M L. Grunwald G K. Astrup A. : The effect of a probiotic milk product on plasma cholesterol: a meta-analysis of short-term intervention studies; Eur J Clin Nutr. 2000; 54(11) 856-860; Renato Sousa, Jaroslava Helper, Jian Zhang, Strephen J Lewis and Wani O Li; Effect of *Lactobacillus acidophilus* supernatants on body weight and leptin expression in rats; BMC complementary and alternative medicine. 2008; 8(5) 1-8]. Recently, with such a variety of physiological activities of lactic acid bacteria becoming known, research has been actively conducted on developing lactic acid bacteria strains that are safe for the human body while having excellent functionality and applying the strains as medicines or functional foods.

Hence, as a result of the endeavor to discover lactic acid bacteria being safe and having excellent immunity-enhancing effects, the inventors of the present disclosure isolated a strain of *Lactobacillus fermentum* subspecies (subsp.) from Hallabong in Jeju Island and confirmed that the strain did not produce biogenic amines while having excellent acid resistance, bile resistance, and immunity-enhancing efficacy (macrophage activity and the like), thereby completing the present disclosure.

DISCLOSURE

Technical Problem

The present disclosure aims to provide a *Lactobacillus fermentum* ATG-V5 strain deposited under accession number KCTC14481BP, an immunity-enhancing pharmaceutical composition containing the same, a food composition, and an immunity-enhancing health functional food containing the food composition.

Technical Solution

The present disclosure provides a *Lactobacillus fermentum* ATG-V5 strain deposited under accession number KCTC14481BP.

In addition, the present disclosure provides an immunity-enhancing pharmaceutical composition characterized by containing the strain.

Furthermore, the present disclosure provides an immunity-enhancing food composition characterized by containing the strain.

Moreover, the present disclosure provides an immunity-enhancing health functional food characterized by containing the food composition.

Advantageous Effects

A *Lactobacillus fermentum* ATG-V5 strain of the present disclosure has no cytotoxicity and has the following immunity-enhancing efficacies: increasing secretion amounts of nitric oxide (NO), interleukin 6 (IL-6), and tumor necrosis factor (TNF) in macrophages, enhancing phagocytosis, reducing a secretion amount of interleukin 1β (IL-1β) in macrophages, enhancing cell viability of splenocytes, increasing secretion amounts of antibodies and cytokines in the blood, and the like. Thus, the strain can be effectively used as a material for an immunity-enhancing pharmaceutical composition and food composition, which can be effectively used in enhancing the immune activities of individuals. In addition, a health functional food characterized by containing the food composition is also effective in enhancing the immune activities of individuals.

DESCRIPTION OF DRAWINGS

FIG. 1 is an image showing a 16S rRNA base sequence (SEQ ID NO: 1) of a *Lactobacillus fermentum* ATG-V5 strain of the present disclosure (hereinafter referred to as a V5 strain);

FIG. 3 is an image showing results of testing whether a V5 strain and a positive control produce biogenic amines;

Figure 14E:
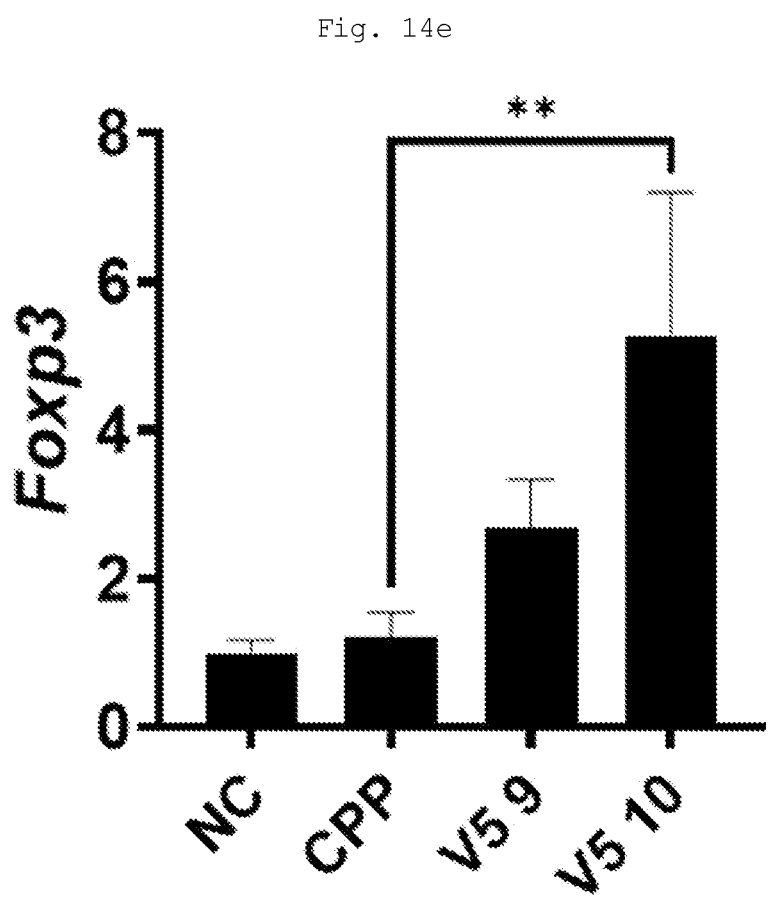

FIG. 14E is a graph showing results of measuring expression levels of forkhead box P3 (FOXP3) mRNA in splenocytes of a CPP-induced animal model by V5 strain administration to identify changes in the differentiation of Treg cells, a T cell subset;

MODE FOR INVENTION

Figure 2:
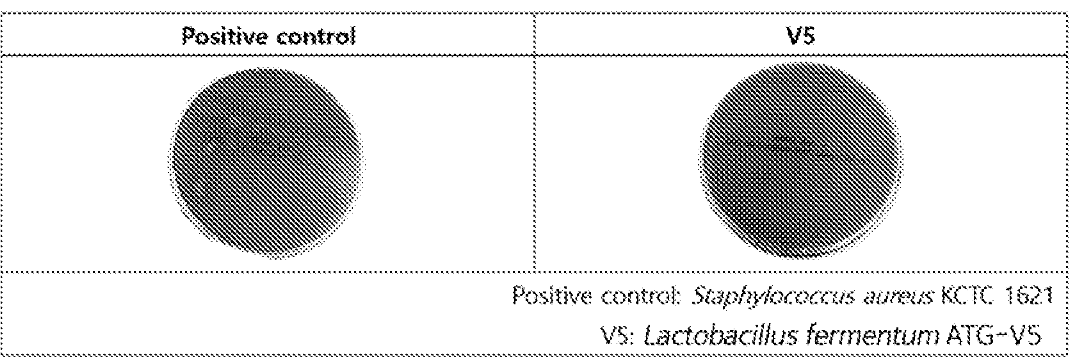
FIG. 2 is an image showing results of confirming whether a V5 strain and a positive control exhibit hemolytic activities.

Hereinafter, the present disclosure will be described in detail.

The present disclosure provides a *Lactobacillus fermentum* ATG-V5 strain deposited under accession number KCTC14481BP.

The strain may be isolated from Hallabong and is preferably isolated from Hallabong in Jeju Island, but is not limited thereto.

The strain may have a 16S rRNA base sequence of SEQ ID NO: 1.

In one embodiment of the present disclosure, as a result of performing 16S rRNA sequencing after isolating *Lactobacillus fermentum* ATG-V5 lactic acid bacteria from Hallabong obtained from Jeju Island on Feb. 8, 2020, a base sequence of SEQ ID NO: 1 obtained through the 16S rRNA sequencing was compared to the BLAST database of NCBI. As a result, the 16S rRNA sequence was 100.0% identical to that of the *Lactobacillus fermentum* strain 8867, confirming that the taxonomic position thereof belongs to *Lactobacillus fermentum*.

The strain may have an immunity-enhancing efficacy. The strain having the immunity-enhancing efficacy may be used for preventing or treating cancer. Such cancers may include at least one selected from the group consisting of breast cancer, colorectal cancer, lung cancer, small cell lung cancer, stomach cancer, liver cancer, blood cancer, bone cancer, pancreatic cancer, skin cancer, head or neck cancer, skin or intraocular melanoma, uterine cancer, ovarian cancer, rectal cancer, anorectal cancer, colon cancer, fallopian tube carcinoma, endometrial carcinoma, cervical cancer, vaginal cancer, vulvar carcinoma, Hodgkin's disease, esophageal cancer, small intestine cancer, endocrine gland cancer, thyroid cancer, parathyroid cancer, adrenal cancer, soft tissue sarcoma, urethral cancer, penile cancer, prostate cancer, chronic or acute leukemia, lymphocytic lymphoma, bladder cancer, kidney cancer, ureteral cancer, renal cell carcinoma, renal pelvic carcinoma, CNS tumor, primary CNS lymphoma, spinal cord tumor, brainstem glioma, and pituitary adenoma.

As one example of the immunity-enhancing efficacy, the strain may increase a secretion amount of nitric oxide (NO) in macrophages.

In one example of the present disclosure, to confirm whether the V5 strain increases the secretion amount of nitric oxide (NO) in macrophages, cells were treated with the strain at concentrations corresponding to ratios of RAW 264.7 cells: the V5 strain of 1:1.25, 1:2.5, 1:5, 1:10, 1:20, and 1:40, and then incubated in a 5% $CO_2$ incubator for 24 hours to induce NO production. As a result, it was confirmed that when treating the V5 strain, the NO production in the RAW 264.7 cells was significantly increased in a concentration-dependent manner (see FIG. 6). In addition, it was confirmed that the V5 strain further induced NO secretion compared to when treating K23 and K24 strains at a strain concentration of 20 (see FIG. 7).

As another example of the immunity-enhancing efficacy, the strain may enhance phagocytosis of macrophages.

In one example of the present disclosure, to confirm whether the V5 strain enhances the phagocytosis of macrophages, cells were treated with the strain at concentrations corresponding to ratios of RAW 264.7 cells: the V5 strain of 1:2.5, 1:5, 1:10, and 1:20, and then the phagocytosis of the RAW 264.7 cells was measured. As a result, it was confirmed that when treating the V5 strain, the phagocytosis in the RAW 264.7 cells was enhanced compared to when treating a control (see FIG. 8).

As another example of the immunity-enhancing efficacy, the strain may increase secretion amounts of interleukin 6 (IL-6) and tumor necrosis factor (TNF) in macrophages and reduce a secretion amount of interleukin 1β (IL-1β).

Figure 9A:
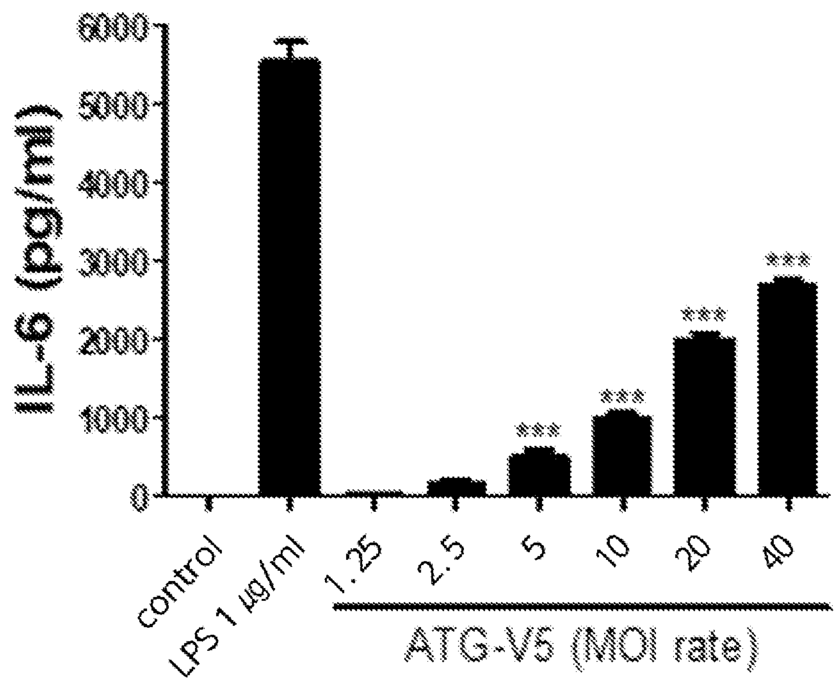
FIG. 9A is a graph showing results of confirming whether a V5 strain increases a secretion amount of interleukin 6 (IL-6) in mouse macrophages, RAW 264.7 cells.
Figure 9B:
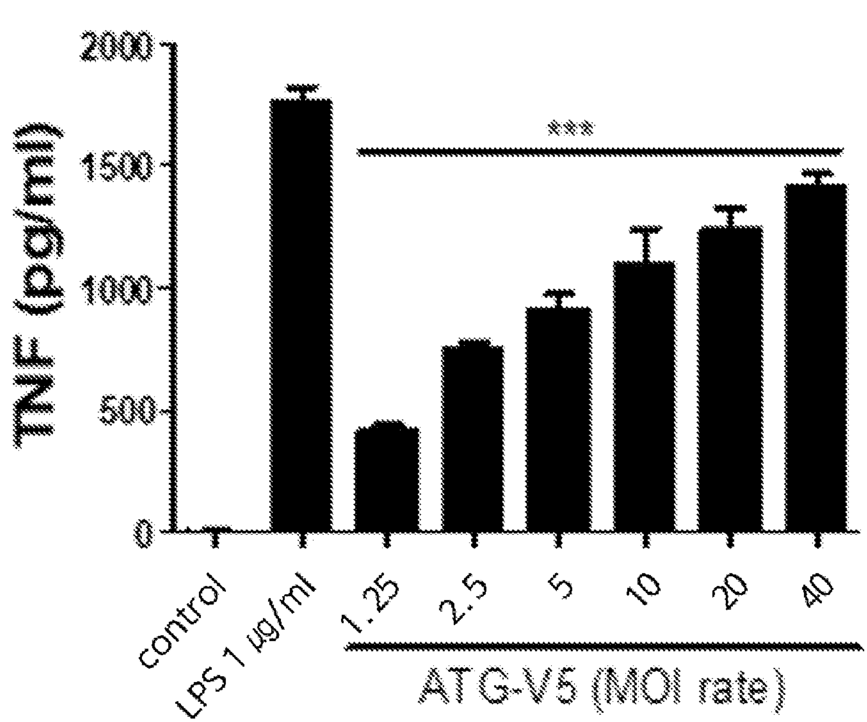
FIG. 9B is a graph showing results of confirming whether a V5 strain increases a secretion amount of tumor necrosis factor (TNF) in mouse macrophages, RAW 264.7 cells.
Figure 9C:
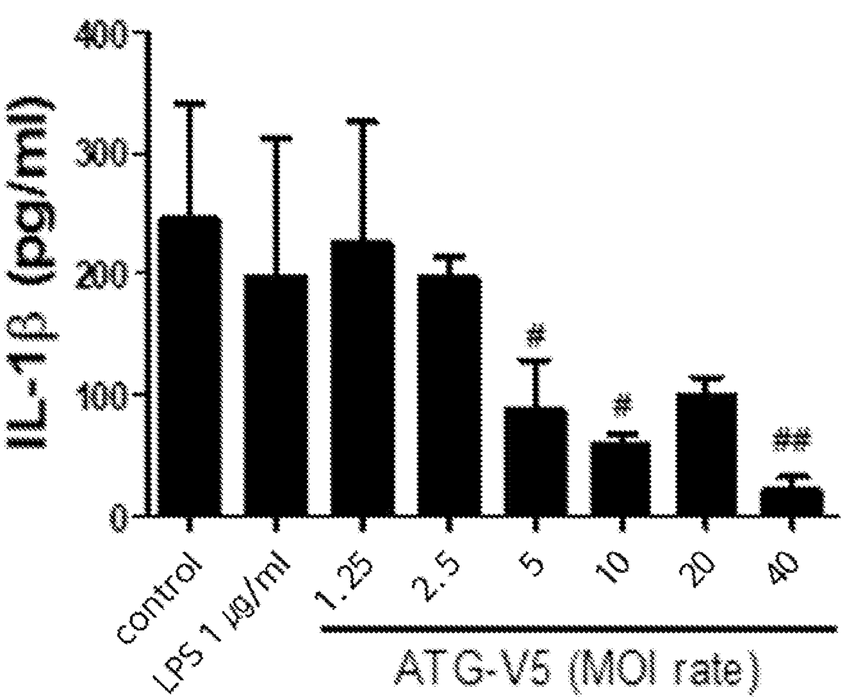
FIG. 9C is a graph showing results of confirming whether a V5 strain reduces a secretion amount of interleukin 1β (IL-1β) in mouse macrophages, RAW 264.7 cells.

In one example of the present disclosure, to confirm effects of the V5 strain on secretion amounts of cytokines in macrophages, cells were treated with the strain at concentrations corresponding to ratios of RAW 264.7 cells: the V5 strain of 1:1.25, 1:2.5, 1:5, 1:10, 1:20, and 1:40, and then enzyme-linked immunosorbent assay (ELISA) for IL-6, TNF-α, IL-1β, and IL-10 was performed. As a result, it was confirmed that the V5 strain increased the amounts of IL-6 and TNF, immunostimulatory cytokines, in a concentration-dependent manner (see FIGS. 9A and 9B) and reduced the amount of IL-1β, contributing to immunoregulation (see FIG. 9C).

As another example of the immunity-enhancing efficacy, the strain may increase the thymus weight of individuals and reduce the spleen weight thereof.

Figure 10:
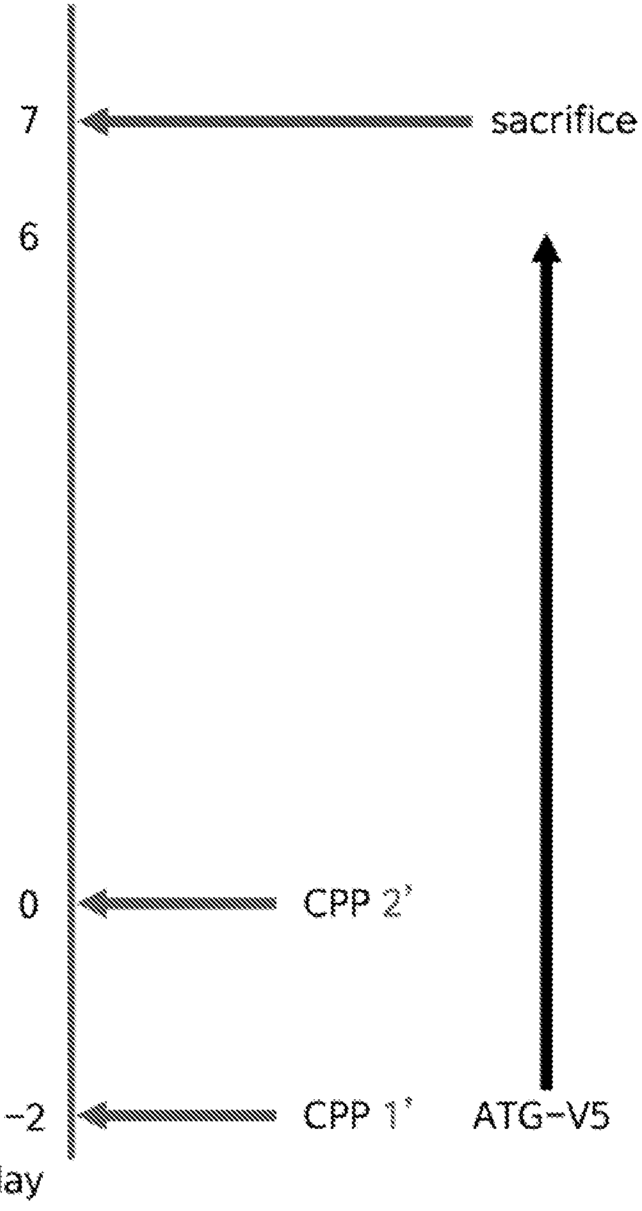
FIG. 10 is a diagram illustrating a test schedule and V5 strain administration conditions using a cyclophosphamide (CPP)-induced animal model.

In one example of the present disclosure, to confirm the immunity-enhancing efficacy of the V5 strain in a cyclophosphamide (CPP)-induced animal model, tests were performed for each concentration of the V5 strain (see FIG. 10). As a result of measuring the thymus and spleen weight of the animal model, it was confirmed that the V5 strain significantly increased the thymus weight from 0.031 g (CPP) to 0.048 g (V5 $10^{10}$ CFU) and significantly reduced the spleen weight from 0.170 g (CPP) to 0.111 g (V5 $10^{10}$ CFU) (see FIGS. 11A and 11B).

As another example of the immunity-enhancing efficacy, the strain may enhance cytotoxicity of natural killer cells (NK cells).

In one example of the present disclosure, to measure the cytotoxicity of the NK cells, splenocytes were obtained from a CPP-induced animal model and then were mixed with YAC-1 cells in a ratio of the YAC-1 cells:the splenocytes of 1:50. As a result of measuring the amount of LDH using an LDH-cell cytotoxicity assay kit, it was confirmed that the V5 strain enhanced the cytotoxicity of the NK cells from 144% (CPP) to 494% (V5 $10^9$ CF-U) and 521% (V5 $10^{10}$ CFU) in the CPP-induced animal model (see FIG. 12).

As another example of the immunity-enhancing efficacy, the strain may enhance cell viability of splenocytes.

In one example of the present disclosure, to measure the cell viability of splenocytes, splenocytes from each mouse were incubated and then treated with WST to measure cell viability. As a result, it was confirmed that the V5 strain enhanced the cell viability of the splenocytes from 99.98% (CPP) to 135.95% (V5 $10^{10}$ CFU) in the CPP-induced animal model (see FIG. 13)

As another example of the immunity-enhancing efficacy, the strain may increase the number of one or more T cell subsets selected from the group consisting of Th1, Th2, Th17, and Treg cells.

In one example of the present disclosure, to confirm changes in differentiation of Th1, Th2, Th17, and Treg cells, the T cells subsets, using mRNA isolated from splenocytes, the mRNA expression levels of the cells were measured. As a result, it was confirmed that CPP suppressed the differentiation of naive T cells, thereby suppressing the total number of T cell subsets, and V5 strain significantly increased the number of Th1, Th2, Th17, and Treg cells (see FIGS. 14A to 14F).

As another example of the immunity-enhancing efficacy, the strain may increase a secretion amount of antibodies in the blood. Preferably, the antibodies are characterized by including IgG and IgA, but are not limited thereto.

Figure 15A:
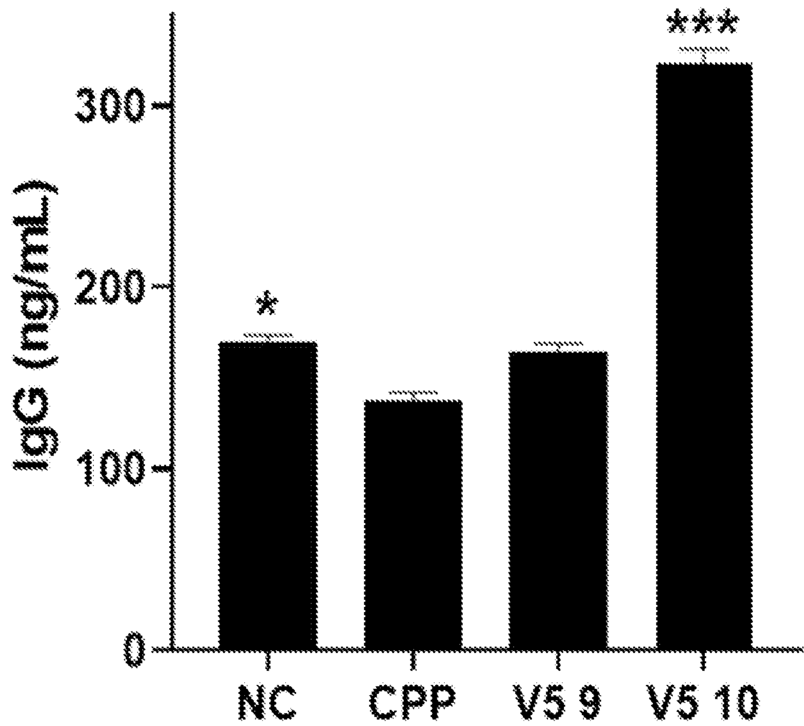
FIG. 15A is a graph showing results of confirming changes in a secretion amount of IgG in the blood of a CPP-induced animal model by V5 strain administration.
Figure 15B:
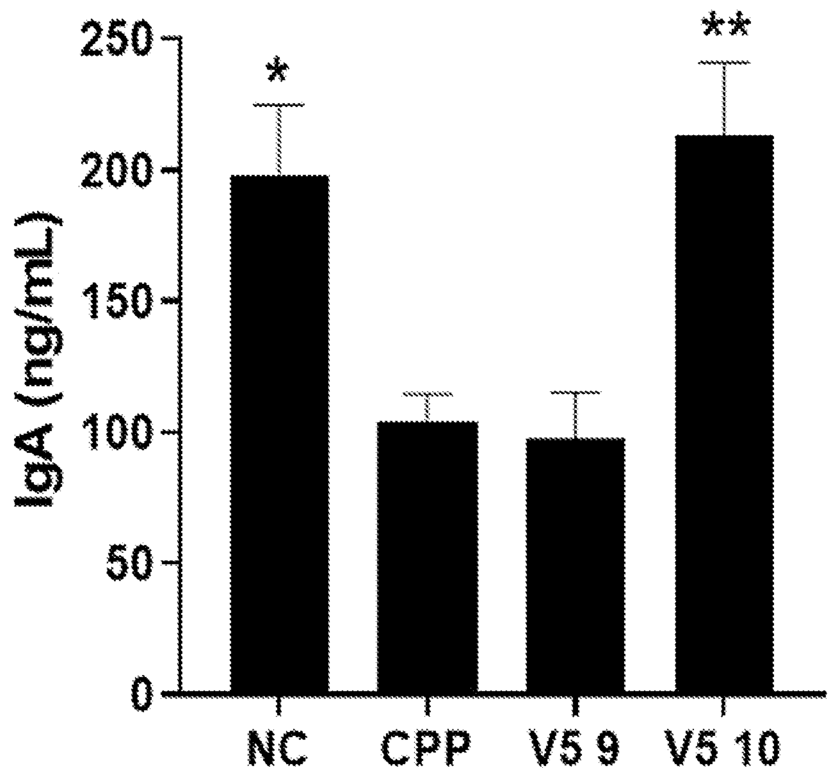
FIG. 15B is a graph showing results of confirming changes in a secretion amount of IgA in the blood of a CPP-induced animal model by V5 strain administration.

In one example of the present disclosure, as a result of analyzing secretion amounts of IgG and IgA in the blood of a CPP-induced animal model, it was confirmed that CPP reduced the secretion amounts of IgG and IgA, and the V5 strain increased the secretion amounts of IgG and IgA (see FIGS. 15A and 15B).

As another example of the immunity-enhancing efficacy, the strain may increase secretion amounts of cytokines in the blood. Preferably, the cytokines are characterized by including one or more cytokines selected from the group consisting of IL-6, interleukin 2 (IL-2), interleukin 10 (IL-10), and interleukin 4 (IL-4), but are not limited thereto.

In one example of the present disclosure, as a result of analyzing cytokines in a CPP-induced animal model, it was confirmed that there was a tendency in which CPP reduced the overall cytokines, and the V5 strain increased the cytokines (see FIG. 16A to 16D).

The strain may further include any one or more selected from the group consisting of culture media, metabolites, and dead cells of the *Lactobacillus fermentum* ATG-V5 strain.

In addition, the present disclosure provides an immunity-enhancing pharmaceutical composition characterized by containing the *Lactobacillus fermentum* ATG-V5 strain. The pharmaceutical composition is effective in the immunity-enhancing efficacy disclosed above. The pharmaceutical composition having the immunity-enhancing efficacy may be used to prevent or treat cancer. Such cancers may include at least one selected from the group consisting of breast cancer, colorectal cancer, lung cancer, small cell lung cancer, stomach cancer, liver cancer, blood cancer, bone cancer, pancreatic cancer, skin cancer, head or neck cancer, skin or intraocular melanoma, uterine cancer, ovarian cancer, rectal cancer, anorectal cancer, colon cancer, fallopian tube carcinoma, endometrial carcinoma, cervical cancer, vaginal cancer, vulvar carcinoma, Hodgkin's disease, esophageal cancer, small intestine cancer, endocrine gland cancer, thyroid cancer, parathyroid cancer, adrenal cancer, soft tissue sarcoma, urethral cancer, penile cancer, prostate cancer, chronic or acute leukemia, lymphocytic lymphoma, bladder cancer, kidney cancer, ureteral cancer, renal cell carcinoma, renal pelvic carcinoma, CNS tumor, primary CNS lymphoma, spinal cord tumor, brainstem glioma, and pituitary adenoma.

The *Lactobacillus fermentum* ATG-V5 strain may be added to the composition of the present disclosure in an amount of 0.001 to 100 wt %.

The pharmaceutical composition may be formulated into oral formulations, such as powders, granules, tablets, capsules, suspensions, emulsions, syrups, aerosols, and the like, external preparations, suppositories, and sterile injection solutions, according to respective common methods, for use. Examples of carriers, excipients, and diluents that may be contained in the pharmaceutical composition may include lactose, dextrose, sucrose, sorbitol, mannitol, xylitol, erythritol, maltitol, starch, gum acacia, alginate, gelatin, calcium phosphate, calcium silicate, cellulose, methylcellulose, microcrystalline cellulose, polyvinylpyrrolidone, water, methylhydroxybenzoate, propylhydroxybenzoate, talc, magnesium stearate, and mineral oil. When being formulated, excipients or diluents, such as commonly used fillers, extenders, binders, wetting agents, disintegrating agents, surfactants, and the like, may be used for preparation. Solid preparations for oral administration may include tablets, pills, powders, granules, capsules, and the like. In addition, such solid preparations are prepared by mixing the strain of the present disclosure or cultures thereof with at least one excipient, for example, starch, calcium carbonate, sucrose or lactose, gelatin, and the like. Not only excipients but also lubricants, such as magnesium stearate and talc, are used. Examples of liquid preparations for oral administration include suspensions, liquid preparations for internal use, emulsions, syrups, and the like. Not only diluents, such as water and liquid paraffin, but also various excipients, such as wetting agents, sweetening agents, aromatics, preservatives, and the like, may be included. Examples of formulations for parenteral administration include sterile aqueous solutions, non-aqueous solvents, suspensions, emulsions, freeze-dried formulations, and suppositories. As for non-aqueous solvents and suspensions, propylene glycol, polyethylene glycol, vegetable oils such as olive oil, injectable esters such as ethyl oleate, and the like may be used. As for suppository bases, WITEPSOL®, macrogol, TWEEN™ 61, cacao fat, laurin fat, glycerogelatin, and the like may be used.

A dosage of the pharmaceutical composition of the present disclosure may vary depending on the age, sex, and weight of a subject to be treated, a specific disease or pathological condition to be treated, the severity of the disease or pathological condition, administration route, and the decision of a prescriber. Dosage determinations based on these factors fall within the level of those skilled in the art. The pharmaceutical composition is typically administered at a dosage in a range of 0.01 mg/kg/day to approximately 2000 mg/kg/day and preferably administered at a dosage of 1 mg/kg/day to 500 mg/kg/day. The pharmaceutical composition may be administered once or multiple times a day. The dosage is not intended to limit the scope of the present disclosure in any way.

Mammals, such as rats, livestock, and humans, may be administered the pharmaceutical composition of the present disclosure through various routes. For example, while all administration methods are envisageable, oral administration, rectal administration, intravenous administration, intramuscular injection, subcutaneous injection, intrauterine injection, or intracerebroventricular injection may be performed. The strain of the present disclosure has little toxicity and side effects and thus is a safely usable medication even when taken for long periods of time for preventive purposes.

In addition, the present disclosure provides an immunity-enhancing food composition characterized by containing the *Lactobacillus fermentum* ATG-V5 strain. The food composition is effective in the immunity-enhancing efficacy disclosed above. The food composition having the immunity-enhancing efficacy may be used to prevent or treat cancer. Such cancers may include at least one selected from the group consisting of breast cancer, colorectal cancer, lung cancer, small cell lung cancer, stomach cancer, liver cancer, blood cancer, bone cancer, pancreatic cancer, skin cancer, head or neck cancer, skin or intraocular melanoma, uterine cancer, ovarian cancer, rectal cancer, anorectal cancer, colon cancer, fallopian tube carcinoma, endometrial carcinoma, cervical cancer, vaginal cancer, vulvar carcinoma, Hodgkin's disease, esophageal cancer, small intestine cancer, endocrine gland cancer, thyroid cancer, parathyroid cancer, adrenal cancer, soft tissue sarcoma, urethral cancer, penile cancer, prostate cancer, chronic or acute leukemia, lymphocytic lymphoma, bladder cancer, kidney cancer, ureteral cancer, renal cell carcinoma, renal pelvic carcinoma, CNS tumor, primary CNS lymphoma, spinal cord tumor, brainstem glioma, and pituitary adenoma.

The *Lactobacillus fermentum* ATG-V5 strain may be added to the food composition of the present disclosure in an amount of 0.001 to 50 wt %. The food composition of the present disclosure may have forms including tablets, capsules, pills, or liquid preparations.

In addition, the present disclosure provides an immunity-enhancing health functional food characterized by containing the food composition. The health functional foods to which the food composition of the present disclosure is addable include, for example, meat, sausages, bread, candy, snacks, noodles, ice cream, dairy products, fermented milk, soup, isotonic beverages, beverages, alcoholic beverages, gum, teas, vitamin complexes, and the like.

Hereinafter, the present disclosure will be described in detail through examples.

However, the following examples of the present disclosure are disclosed only for illustrative purposes and should not be construed as limiting the present disclosure.

<Example 1> Isolation and Identification of Lactic Acid Bacteria for Functionality Evaluation <1-1> Sequencing of V5 Strain 16S rRNA

*Lactobacillus fermentum* ATG-V5 lactic acid bacteria were isolated from Hallabong obtained from Jeju Island on Feb. 8, 2020.

Specifically, the resulting product obtained by diluting the Hallabong with 0.9% saline using a 10-fold serial dilution method was spread on a de Man Rogosa Sharpe (MRS) medium and then incubated at 37° C. for 48 hours. Next, colonies of lactic acid bacteria generated in the incubated MRS medium were microscopically observed to pick one having a *bacillus* form and not responding to catalase, which was later named an ATG-V5 strain (hereinafter referred to as V5 strain).

A request was made to Solgent (Daejeon) for the sequencing of V5 strain 16S rRNA. Using 27F (5'-AGA GTT TGA TCC TGG CTC AG-3'), 518F (5'-CCA GCA GCC GCG GTA ATA C-3'), 907R (5'-CCG TCA ATT CMT TTR AGT TT-3'), and 1492R (5'-GGT TAC CTT GTT ACG ACT T-3') as primers for sequencing, base sequences were read four times. Then, a base sequence contig derived from base sequence alignment in each reading was analyzed using the BLAST online tool (blast.ncbi.nlm.nih.gov/Blast.cgi) of the National Center for Biotechnology Information (NCBI).

As a result of comparing the base sequence of SEQ ID NO: 1 below obtained through 16S rRNA sequencing to the BLAST database of NCBI, the 16S rRNA sequence was 100.0% identical to that of the *Lactobacillus fermentum* strain 8867, confirming that the taxonomic position thereof belonged to *Lactobacillus fermentum.*

Hence, the strain of the present disclosure (accession number: KCTC14481BP) was deposited at the Korean Collection for Type Cultures (KCTC) on Mar. 4, 2021.

<1-2> Confirmation of Sugar Fermentation Pattern of V5 Strain

To identify and characterize sugar fermentation patterns, the API 50 CH test (BioMerieux, France) was performed.

Specifically, pure cultured lactic acid bacteria were suspended in a 10-mL API 50 CHL medium (BioMerieux, France) to an $OD_{600}$ absorbance of approximately 0.5. Then, the suspension culture medium was inoculated into each ampoule of an API 50 CH test strip and incubated at 37° C. The results of sugar fermentation were confirmed 24 and 48 hours after inoculation.

As a result of examining the glycolytic ability of the V5 strain, mannose and D-gluconate showed a weak positive reaction (blue turns green within 48 hours), and ribose, galactose, fructose, maltose, lactose, melibiose, sucrose, and raffinose showed a positive reaction (blue turns yellow within 48 hours) (Table 1).

TABLE 1

| Carbohydrates | *Lactobacillus fermentum* ATG-V5 |
|---|---|
| Glycerol | − |
| Erythritol | − |
| D-Arabinose | − |
| L-Arabinose | − |
| Ribose | + |
| D-Xylose | − |
| L-Xylose | − |
| Adonitol | − |
| Methyl-βanoside | − |
| Galactose | + |
| Glucose | + |
| Fructose | + |
| Mannose | w |
| Sorbose | − |
| Rhamnose | − |
| Dulcitol | − |
| Inositol | − |
| Mannitol | − |
| Sorbitol | − |
| Methyl-αD-Mannopyranoside | − |
| Methyl-αD-Glucopyranoside | − |
| N-Acetylglucosamine | − |
| Amygdalin | − |
| Arbutin | − |
| Esculin | − |
| Salicin | − |
| Cellbiose | − |
| Maltose | + |
| Lactose | + |
| Melibiose | + |
| Sucrose | + |
| Trehalose | − |
| Inulin | − |
| Melezitose | − |
| Raffinose | + |
| Starch | − |
| Glycogen | − |
| Xylitol | − |
| Gentiobiose | − |
| Turanose | − |
| Lyxose | − |
| Tagatose | − |
| D-Fructose | − |
| D-Arabitol | − |
| L-Arabitol | − |
| Gluconate | w |
| 2-keto-Gluconate | − |
| 5-keto-Gluconate | − |

*Sugar fermentation patterns of *Lactobacillus fermentum* ATG-V5 (positive: +, weak positive: w, negative: −)

<Example 2> Confirmation of V5 Strain Characteristics

<2-1> Confirmation of Antibiotic Resistance Safety of V5 Strain

In antibiotic testing, e-test strips (BioMerieux, France) for nine types of antibiotics, ampicillin, vancomycin, gentamicin, kanamycin, streptomycin, clindamycin, erythromycin, tetracycline, and chloramphenicol, were used to confirm the minimum inhibitory concentration (MIC) value.

Specifically, the V5 strain was suspended to an OD600 absorbance of approximately 0.8 and then spread on an MRS solid medium using a sterile cotton swab. The solid medium on which the strain was spread was dried for about three minutes and then incubated at 37° C. for 24 hours by placing each E-test strip thereon. However, lactic acid bacteria may naturally develop natural intrinsic resistance to gentamicin, kanamycin, and streptomycin, based on aminoglycoside, due to the nature thereof. Thus, as a test medium for those antibiotics, a plate count agar (PCA, Difco Laboratories, USA) or Mueller-Hinton agar (MHA, Difco Laboratories, USA) was used. The standards for the types of antibiotics and the minimum inhibitory concentration enabled to be determined safe were referred to the guidelines published by the European Food Safety Authority (EFSA) (EFSA Panel on Additives and Products or Substances Used in Animal Feed, 2012).

As a result of performing a test to measure the minimum inhibitory concentration (MIC) of the V5 strain against the nine types of antibiotics, it was confirmed that the V5 strain had an antibiotic susceptibility lower than the limit of the EFSA guidelines (Table 2).

TABLE 2

| Organism | AMP | VAN | GEN | KAN | STR |
|---|---|---|---|---|---|
| *Lactobacillus fermentum* ATG-V5 | 0.125 | NR | 2 | 12 | 12 |
| EFSA standards | 4 | NR | 8 | 64 | 64 |

| Organism | CD | ERY | TET | CM |
|---|---|---|---|---|
| *Lactobacillus fermentum* ATG-V5 | 0.094 | 0.19 | 2 | 4 |
| EFSA standards | 1 | 1 | 16 | 4 |

The units for each numerical value are μg/mL,
AMP, ampicillin;
VAN, vancomycin;
GEN, gentamicin;
KAN, kanamycin;
STR, Streptomycin;
CD, clindamycin;
ERY, erythromycin;
TET, tetracycline;
CM, Chloramphenicol; and
NR, not required.

<2-2> Confirmation of Hemolysis of V5 Strain

To determine whether the V5 strain exhibited hemolytic activity regarding the safety of probiotics, the V5 strain was inoculated into a medium (BAPI, Asan Pharmaceutical) containing 5% sheep blood and then incubated at 37° C. for 24 to 48 hours.

As a result, growth of the V5 strain was confirmed in the solid medium, but the hemolytic activity and clear zones resulting therefrom were not found (FIG. 2).

<2-3> Confirmation of Biogenic Amine Production in V5 Strain

To confirm whether the V5 strain produced biogenic amines, such as histamine, tyramine, putrescine, and cadaverine, that may be harmful to the human body, a test was performed according to the method suggested by Bover-Cid and Holzapfel (Bover-Cid and Holzafel, 1999).

Specifically, after constructing a medium according to the components of the solid medium for testing presented in "Bover-Cid and Holzapfel, 1999", the V5 strain was inoculated and incubated at 37° C. for 72 hours to observe changes in the color of the medium. When the biogenic amines are positive, the pH value around the periphery to which the V5 strain is inoculated is increased due to the activity of decarboxylase, so the bromocresol purple reagent contained in the medium turns from yellow to purple.

Figure 3:
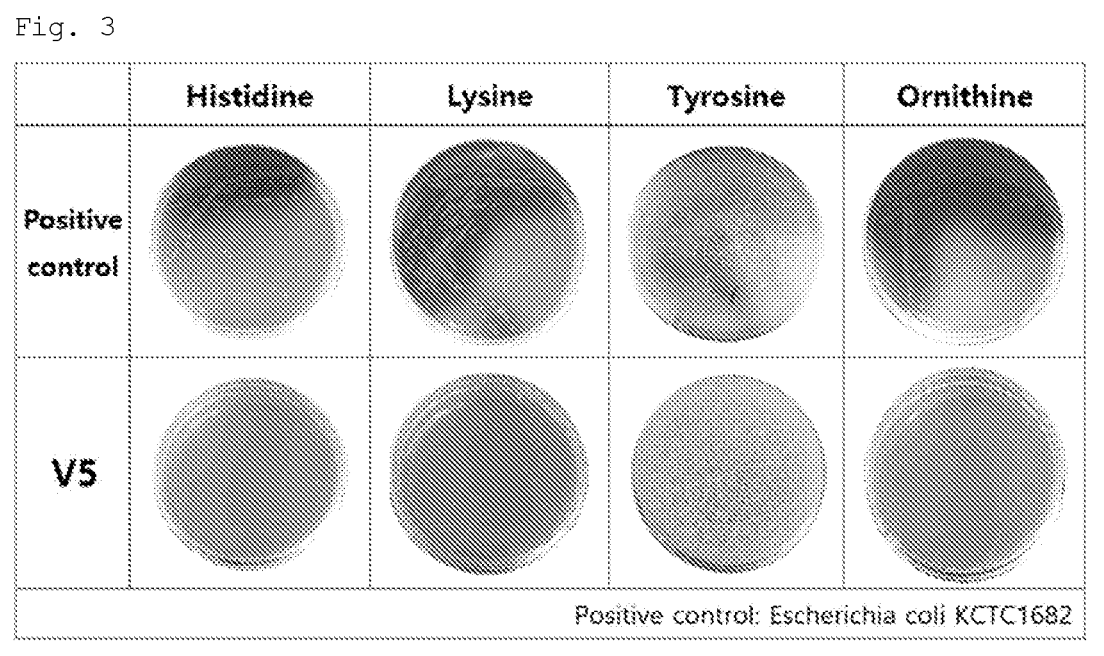

As a result, although the V5 strain was confirmed to be grown in the solid medium, no color changes were found, confirming that not a single one or more biogenic amine among histamine, tyramine, putrescine, and cadaverine was not produced (FIG. 3).

<2-4> Confirmation of Antibacterial Effect of V5 Strain

A total of seven types of infectious or opportunistic infectious bacteria, such as four gram-positive types, *Staphylococcus aureus* (SA, KCTC1621), *Listeria monocytogenes* (LM, KCTC3569), *Streptococcus mutans* (SM, KCTC3065), and *Streptococcus salivarius* (SS, ATG-P1), and three gram-negative types, *Escherichia coli* (EC, KCTC1682), *Pseudomonas aeruginosa* (PA, KCTC2004), and Cronobacter sakazakii (CS, KCTC2949), were used to perform a disc test.

Specifically, the seven types of bacteria incubated overnight on a BHI plate medium were each independently suspended in 1× phosphate-buffered saline (PBS) to an $OD_{600}$ of about 0.8. Then, each suspension was absorbed using a sterile cotton swab, overall spread on an agar medium where BHI and MRS were mixed in a ratio of 1:1 for testing the antibacterial activity of lactic acid bacteria, and then dried for about three minutes. An 8-mm paper disc (Advantec, Japan) was attached to the dried agar medium for testing. Next, 35 μL of each V5 solution incubated in MRS broth was inoculated into the paper disc for about 18 to 20 hours, dried for about three minutes, and incubated at 37° C. to observe the process. The size of the clear zone formed after incubation was calculated as the final value by measuring the diameter and subtracting 8 mm, the diameter of the paper disc.

As a result of measuring the antibacterial activity of the V5 strain against the seven types of infectious or opportunistic infectious bacteria, it was confirmed that the V5 strain had an antibacterial effect against the six types of opportunistic bacteria, excluding SS (Table 3).

TABLE 3

| Organism | SA | LM | SM | SS | EC | PA | CS |
|---|---|---|---|---|---|---|---|
| *Lactobacillus fermentum* ATG-V5 | 4 | 6 | 4 | 0 | 4 | 10 | 4 |

SA, *Staphylococcus aureus* KCTC1621;
LM, *Listeria monocytogenes* KCTC3569;
SM, *Streptococcus mutans* KCTC3065;
SS, *Streptococcus salivarius* ATG-P1;
EC, *Escherichia coli* KCTC1682,
PA, *Pseudomonas aeruginosa* KCTC2004; and
CS, *Cronobacter sakazakii* KCTC2949

<2-5> Confirmation of Acid Resistance and Bile Resistance of V5 Strain

When ingested with food, lactic acid bacteria reside in the stomach, which secretes strong gastric acid, for about one hour, reside in highly concentrated bile in the duodenum for about two hours, and then move to the intestines. It is known that lactic acid bacteria serve as probiotics by being attached to the intestines and providing benefits to hosts only when being survivable in such intense environments and enter the intestines. Thus, acid resistance and bile resistance tests were performed on the V5 strain isolated by a simulated stomach duodenum passage (SSDP) method where conditions thereof were set to be similar to the environment of the human body (stomach and duodenum).

Specifically, the V5 strain was incubated in an MRS liquid medium for 18 hours. Then, 1 mL of the strain solution was placed in a sterile disposable tube and centrifuged under the following conditions: 12,000 ×g, 4° C., and 5 minutes. Next, the supernatant was discarded, and a process of washing the cell pellet with physiological saline was repeatedly performed twice. Then, after removing the physiological saline, the precipitated V5 strain was mixed in 10 mL of an MRS liquid medium adjusted to a pH of 2 and thoroughly blended. The CFU/mL of the initial bacteria was counted by taking 1 mL of the suspension, followed by 10-fold serial dilution, and spreading the diluted suspension on an MRS solid medium for counting. Then the remaining 9 mL was continuously mixed with 1.5 mL of bile acid (100 mL of distilled water was mixed in 10 g oxgall and sterilized under high pressure for use) and 17 mL of duodenum juice (6.4 g/L $NaHCO_3$, 0.239 g/L KCl, and 1.28 g/L NaCl were mixed in distilled water and sterilized to a pH of 7.4 under high pressure for use). Next, the total volume was adjusted to 30 mL using MRS and then incubated in a 37° C. incubator for two hours. After two hours, 1 mL of the culture medium was taken, 10-fold diluted serially, and spread on an MRS solid medium to count the number of surviving bacteria. The CFU/mL of the initial bacteria counted was compared with the CFU/mL of the bacteria remaining alive after three hours to calculate the survival rate.

As a result, it was confirmed that the V5 strain had a survival rate of 92% at a pH of 2.0. In addition, a survival rate of 0.05% was confirmed when treated with the duodenal juice and 0.5% oxgall (Table 4). This indicates that the V5 strain may sufficiently survive under gastric acid conditions.

TABLE 4

| | Initial cell number (log CFU/mL) | After one hour at pH 2.0 (log CFU/mL) | Survival rate (%) after one hour at pH 2.0 | After two or more hours in 0.5% oxgall (log CFU/mL) | Total survival rate (%) |
|---|---|---|---|---|---|
| V5 | 8.70 ± 0.09 | 8.67 ± 0.04 | 92.2 | 5.39 ± 0.20 | 0.05 |

<2-6> Whole-Genome Sequencing of V5 Strain

For whole-genome sequencing of the V5 strain, genomic DNA of the V5 strain was extracted, and the base sequence was analyzed using the single-molecule real-time (SMRT) sequencing technique of Pacific Bioscience. The produced sequence data was assembled using the hierarchical genome-assembly process (HAGP) 2 protocol of the SMRT analysis software v2.3.0, and the Rapid Annotation using Subsystem Technology (RAST) server (rast.nmpdr.org/) was used for annotation. In addition, average nucleotide identity (ANI) analysis was performed to confirm the similarity between known *Lactobacillus reuteri* strains, and whether the V5 strain was safe was verified once more on the basis of the genetic information using PathoFinder 1.1 (cge.cbs.dtu.dk/services/PathogenFinder/).

Figure 4:
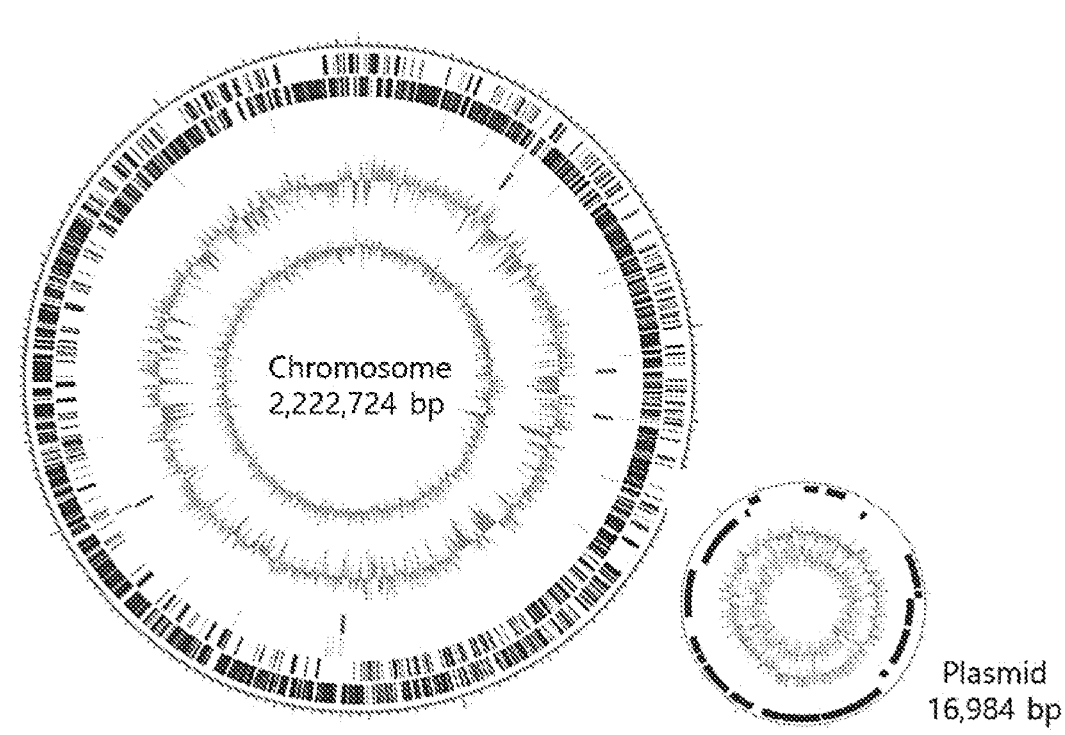
FIG. 4 is an image showing a completely sequenced genome map of a V5 strain (2,222,724-bp chromosomes and 16,984-bp plasmid)

As a result of analyzing the genome information of the V5 strain, 2,222,724-bp chromosomes and 16,984-bp plasmid were obtained (FIG. 4). In addition, as a result of strain identification using the 16S rRNA gene sequence on the genome, the V5 strain was identified as *Lactobacillus fermentum* species.

To confirm the novelty of the V5 strain in the annotation results, ANI analysis was performed using the V5 strain and eight strains having genome sizes similar to that of the type strain of *Lactobacillus fermentum* species and having completely sequenced genome information. As a result, the genome sizes of the strains were all different and showed a difference of 0.45 to 2.37%, confirming that the V5 strain was a novel strain that had previously been unknown (Table 5).

TABLE 5

| Strain | Size (bp) | ANI | Assembly level | Release Date |
|---|---|---|---|---|
| ATG-V5 | 2,239,708 | Corresponding strain | Complete | Undisclosed |
| DSM 20052 (type strain) | 1,887,974 | 99.27 | Scaffold | 2020 Jul. 8 |
| LMT2-75 | 2,298,221 | 99.13 | Complete | 2018 Dec. 2 |
| 3872 | 2,297,851 | 99.26 | Complete | 2015 Jun. 17 |
| FTDC 8312 | 2,239,921 | 99.38 | Complete | 2017 May 9 |
| AGR 1485 | 2,226,862 | 98.89 | Complete | 2020 Feb. 27 |
| SNUV175 | 2,176,678 | 99.03 | Complete | 2017 Jan. 10 |
| CECT 5716 | 2,100,449 | 99.55 | Complete | 2010 Jun. 29 |

TABLE 5-continued

| Strain | Size (bp) | ANI | Assembly level | Release Date |
|---|---|---|---|---|
| SK152 | 2,092,273 | 99.01 | Complete | 2017 Aug. 7 |
| AGR 1487 | 1,939,032 | 97.63 | Complete | 2020 Feb. 27 |

As a result of categorizing the coding sequence on the basis of the annotated information, the V5 strain had 119 genes related to carbohydrate transport and metabolism and 85 genes related to cell wall, membrane, and envelope biogenesis among a total of 2,100 functional genes, confirming that a probiotic efficacy was able to be exhibited (Table 6).

In addition, as a result of looking into the genetic safety of the V5 strain using PathoFinder, it was confirmed that the V5 strain was not pathogenic, confirming that industrialization thereof was unproblematic.

TABLE 6

| Predicted function | Gene count |
|---|---|
| Translation, ribosomal structure and biogenesis | 135 |
| RNA processing and modification | 0 |
| Transcription | 115 |
| Replication, recombination and repair | 334 |
| Chromatin structure and dynamics | 0 |
| Cell cycle control, cell division, chromosome partitioning | 21 |
| Nuclear structure | 0 |
| Defense mechanisms | 33 |
| Signal transduction mechanisms | 44 |
| Cell wall/membrane/envelope biogenesis | 85 |
| Cell motility | 4 |
| Cytoskeleton | 0 |
| Extracellular structures | 0 |
| Intracellular trafficking, secretion, and vesicular transport | 18 |
| Posttranslational modification, protein turnover, chaperones | 52 |
| Energy production and conversion | 82 |
| Carbohydrate transport and metabolism | 119 |
| Amino acid transport and metabolism | 183 |
| Nucleotide transport and metabolism | 91 |
| Coenzyme transport and metabolism | 64 |
| Lipid transport and metabolism | 47 |
| Inorganic ion transport and metabolism | 87 |
| Secondary metabolites biosynthesis, transport and catabolism | 13 |
| General function prediction only | 123 |
| Function unknown | 460 |

<Example 3> Confirmation of Efficacy of V5 Strain on Proliferating Macrophage and Enhancing Function <3-1> Confirmation of Proliferation Ability of Macrophages by V5 Strain To confirm the proliferative ability of macrophages by the V5 strain, RAW 264.7 cells, mouse macrophages used as representative immune cells, were used.

Specifically, the RAW 264.7 cells were incubated in a 96-well plate at $3\times10^4$ cells/well. Then, to treat the V5 strain with a predetermined amount of the cells in a predetermined ratio, the number of bacteria was calculated in a ratio of the multiplicity of infection (MOI), and the V5 strain was treated. The cells were treated with the strain at concentrations corresponding to ratios of the RAW 264.7 cells: the V5 strain of 1:1.25, 1:2.5, 1:5, 1:10, 1:20, and 1:40 and incubated for 24 hours to measure the proliferative ability of the RAW 264.7 cells at an absorbance of 450 nm using WST substrate (DoGenBio, KR).

Figure 5:
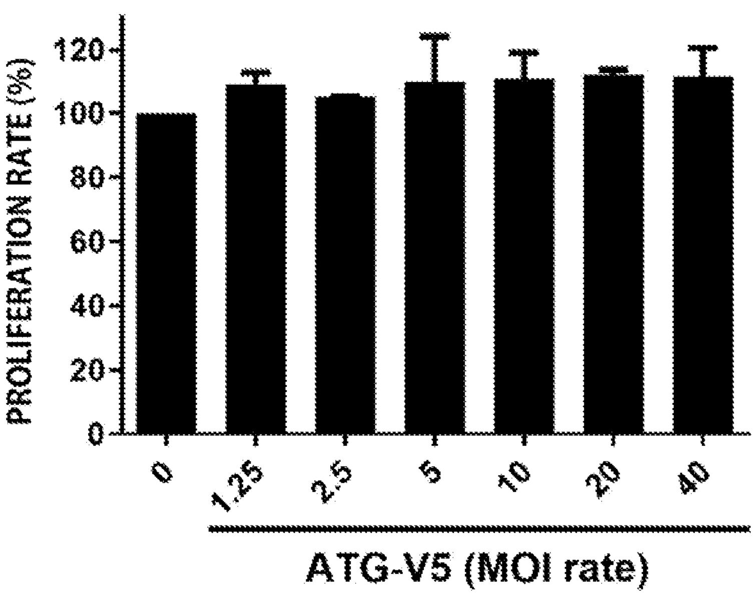
FIG. 5 is a graph showing results of testing whether a V5 strain proliferates mouse macrophages, RAW 264.7 cells.

As a result, it was confirmed that although there was little difference in the level of proliferation of macrophages by the V5 strain, no cytotoxicity was exhibited by the V5 strain (FIG. 5).

<3-2> Confirmation of Increased NO Secretion Amount in Macrophages by V5 Strain

To determine whether the V5 strain increased a secretion amount of nitric oxide (NO) in macrophages, RAW 264.7 cells were incubated in a 96-well plate at $3\times10^4$ cells/well for 24 hours in a 5% $CO_2$ incubator. The cells were treated with the strain at concentrations corresponding to ratios of the Raw 264.7 cells: the V5 strain of 1:1.25, 1:2.5, 1:5, 1:10, 1:20, and 1:40 and incubated in a 5% $CO_2$ incubator for 24 hours to induce NO production. As a positive control, 1 μg/mL LPS was used. After mixing 50 μL of the supernatant incubated for 24 hours and 50 μL of a Griess reagent (Sigma, USA), the reaction was performed for 15 to 30 minutes, followed by measurement at an absorbance of 540 nm.

Figure 6:
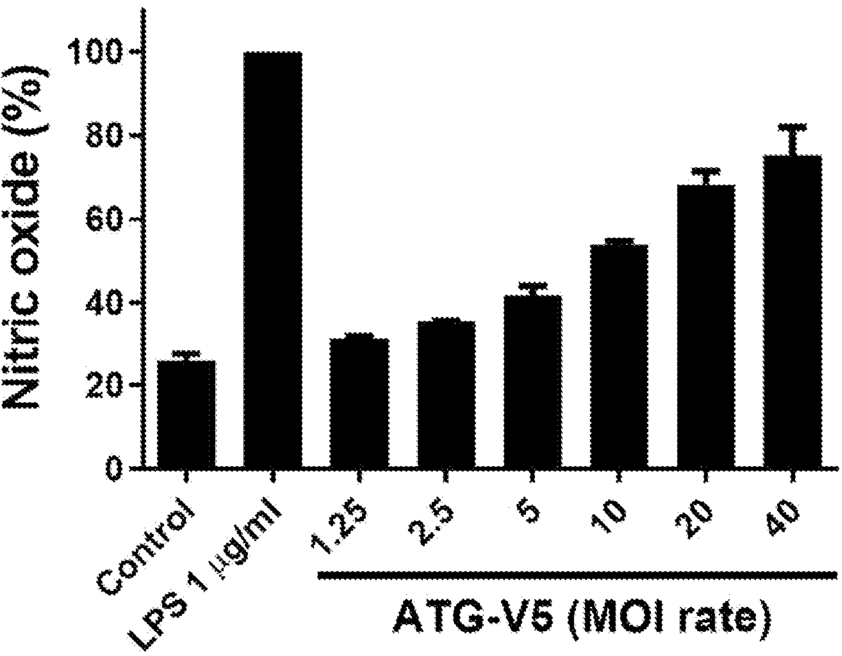
FIG. 6 is a graph showing results of testing whether a V5 strain increases a secretion amount of nitric oxide (NO) in mouse macrophages, RAW 264.7 cells.

As a result, it was confirmed that when treating the V5 strain, the NO production in the RAW 264.7 cells was significantly increased in a concentration-dependent manner (FIG. 6).

<3-3> Comparison of Efficacies of V5 Strain and Other Strains on Increasing NO Secretion Amount in Macrophages RAW 264.7 cells were incubated in a 96-well plate at $3\times10^4$ cells/well for 24 hours in a 5% $CO_2$ incubator. The cells were treated with the strain at concentrations corresponding to ratios of the RAW 264.7 cells: a V5, K23, or K24 strain of 1:10 and 1:20 and incubated in a 5% $CO_2$ incubator for 24 hours to induce NO production. As a positive control, 1 μg/mL LPS was used. After mixing 50 μL of the supernatant incubated for 24 hours and 50 μL of a Griess reagent (Sigma, USA), the reaction was performed for 15 to 30 minutes, followed by measurement at an absorbance of 540 nm.

Figure 7:
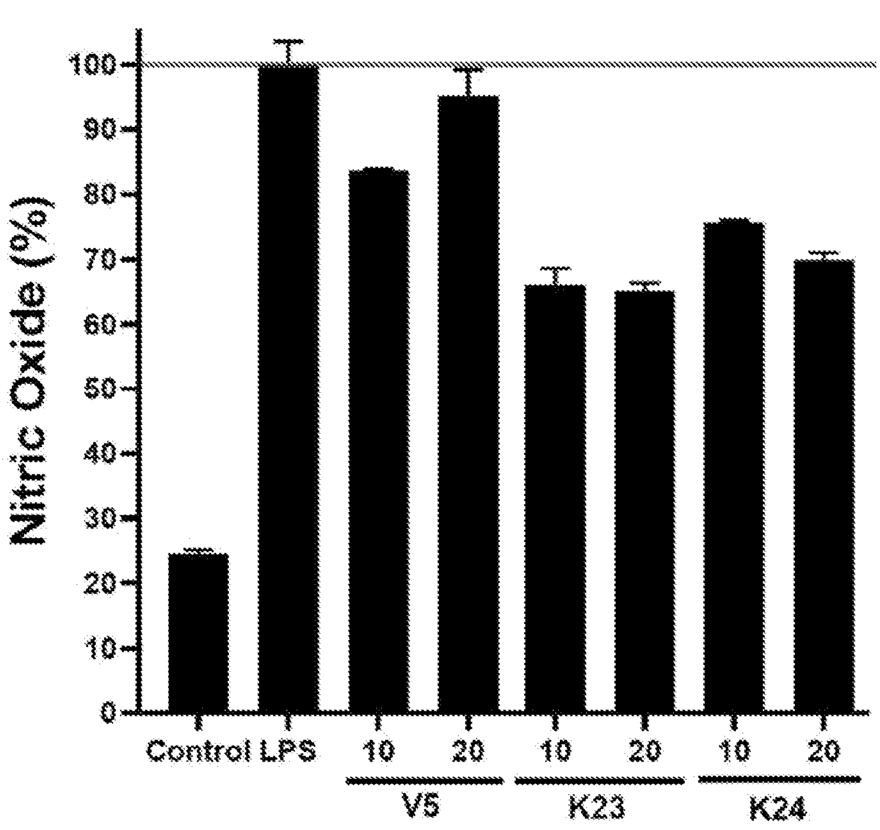
FIG. 7 is a graph showing results of comparing the degrees to which V5, K23, and K24 strains increase secretion amounts of NO in mouse macrophages, RAW 264.7 cells.

As a result of comparing the secretion amount of nitric oxide (NO) by treating *Lactobacillus fermentum* ATG-V5 (V5 strain), ATG-K23 (K23 strain), and ATG-K24 (K24 strain), NO was confirmed to be secreted by the V5, K23, and K24 strains. However, it was confirmed that the V5 strain increased NO in a concentration-dependent manner. In addition, it was confirmed that the V5 strain (95.1%) further induced NO secretion compared to when treating the K23 (65.2%) and K24 strains (69.9%) at a strain concentration of 20 (FIG. 7).

<3-4> Confirmation of Phagocytosis of Macrophages Enhanced by V5 Strain

In addition, to confirm whether the V5 strain enhanced phagocytosis of macrophages, RAW 264.7 cells were incubated in a 96-well plate at $5\times10^4$ cells/well. The cells were treated with the strain at concentrations corresponding to ratios of the RAW 264.7 cells: the V5 strain of 1:2.5, 1:5, 1:10, and 1:20, treated with a Zymosan substrate to measure the phagocytosis of the RAW 264.7 cells, and then incubated for two hours. "Inhibitor" was used as a control to confirm whether the phagocytosis induced the test, and the intake of the Zymosan substrate by the RAW 264.7 cells was measured at an absorbance of 405 nm.

Figure 8:
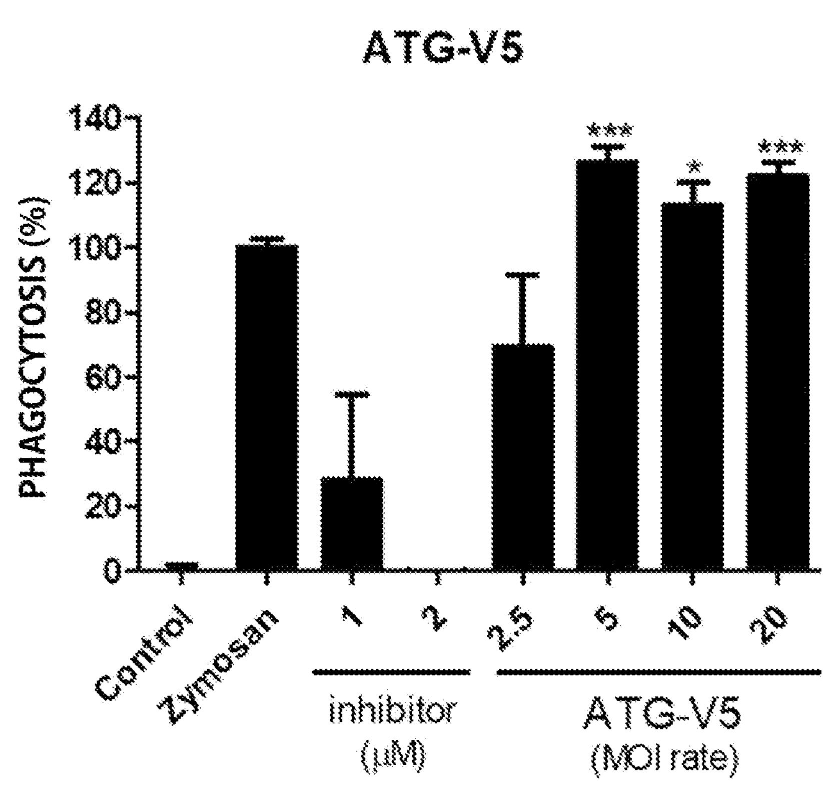
FIG. 8 is a graph showing results of testing whether a strain V5 enhances phagocytosis of mouse macrophages, RAW 264.7 cells.

As a result, it was confirmed that when treating the V5 strain, phagocytosis increased in the RAW 264.7 cells compared to when treating the control (FIG. 8).

<3-5> Confirmation of Effect of V5 Strain on Secretion Amounts of Cytokines in Macrophages To confirm the effect of the V5 strain on secretion amounts of cytokines in macrophages, RAW 264.7 cells were incubated in a 96-well plate at $3\times10^4$ cells/well for 24 hours in a 5% $CO_2$ incubator. The cells were treated with the strain at concentrations corresponding to ratios of the Raw 264.7 cells: the V5 strain of 1:1.25, 1:2.5, 1:5, 1:10, 1:20, and 1:40 and incubated in a 5% $CO_2$ incubator for 24 hours to induce cytokine production. As a positive control, 1 μg/mL LPS was used, and enzyme-linked immunosorbent assay (ELISA) for IL-6, TNF-α, IL-1β, and IL-10 was performed using the supernatant incubated for 24 hours.

Figure 9D:
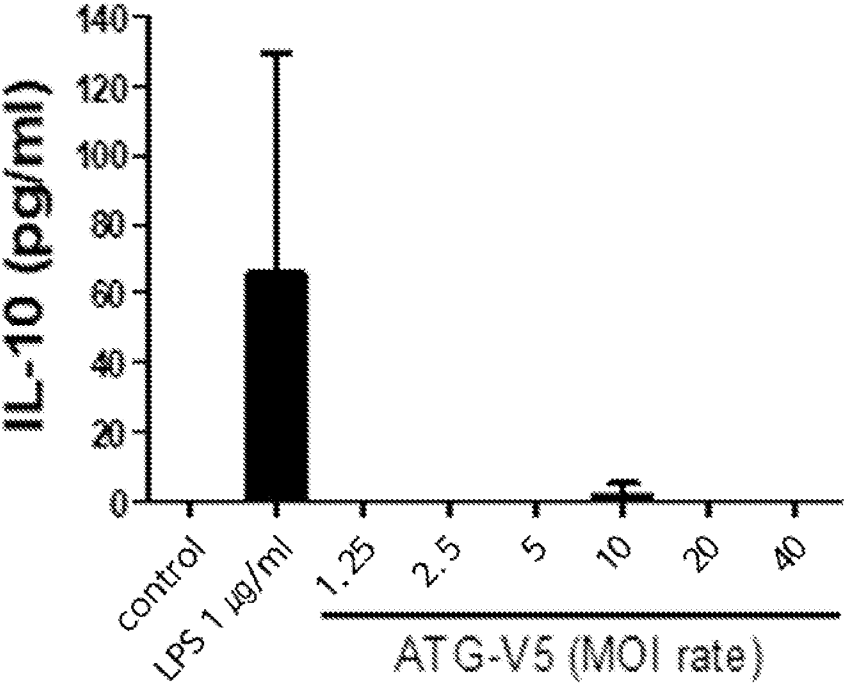
FIG. 9D is a graph showing results of confirming whether a V5 strain increases a secretion amount of interleukin 10 (IL-10) in mouse macrophages, RAW 264.7 cells.

As a result, it was confirmed that the V5 strain increased the IL-6 and TNF, immunostimulatory cytokines, in a concentration-dependent manner (FIGS. 9A and 9B), reduced the amount of IL-1β, contributing to immunoregulation (FIG. 9C), and did not induce the secretion of IL-10, an immunosuppressive cytokine (FIG. 9D).

<Example 4> Confirmation of Immunity-Enhancing Efficacy of V5 Strain in CPP-Induced Animal Model <4-1> Test Schedule and V5 Strain Administration Conditions To confirm the immunity-enhancing efficacy of the V5 strain in a cyclophosphamide (CPP)-induced animal model, tests were performed for each concentration of the V5 strain. Cyclophosphamide (CPP) is an anticancer drug widely used for all types of cancers, sarcomas, leukemia, and malignant lymphoma, and is a non-specific immunosuppressant. The potential of test substances, such as probiotics, being usable as immunity-enhancing materials was able to be evaluated by measuring the immunity-enhancing activity of mice whose immune systems were suppressed by CPP treatment. When CPP suppresses immunity, the weight of the thymus, an immune tissue, and the number of thymocytes are reduced, and the spleen weight is increased as a result of a defense mechanism against immunosuppression. In addition, overall declined immune function, including reduced differentiation of T cells and B cells, reduced phagocytosis of macrophages, reduced secretion of cytokines, which are immunity-activating substances, reduced NK cell activity, and the like, are exhibited.

The test was performed in the following four groups with seven mice per group: a normal control (NC), a group treated with 150 mg/kg of CPP, a group treated with $1\times10^9$ CFU/mouse ($10^9$ CFU) ATG-V5 (V5 strain), and a group treated with $1\times10^{10}$ CFU/mouse (V5 $10^{10}$ CFU) ATG-V5 (V5 strain). During the test period, ATG-V5 was orally administered on a daily basis starting from the primary CPP induction (−2 day), and dissection was performed on the 7th day (FIG. 10).

<4-2> Confirmation of Weight Changes in Thymus and Spleen In CPP-Induced Animal Model by V5 Strain Administration To confirm the effect of the V5 strain on the weight of the thymus and spleen of a CPP-induced animal model, the weight of the thymus and spleen of the animal model was measured.

Figure 11A:
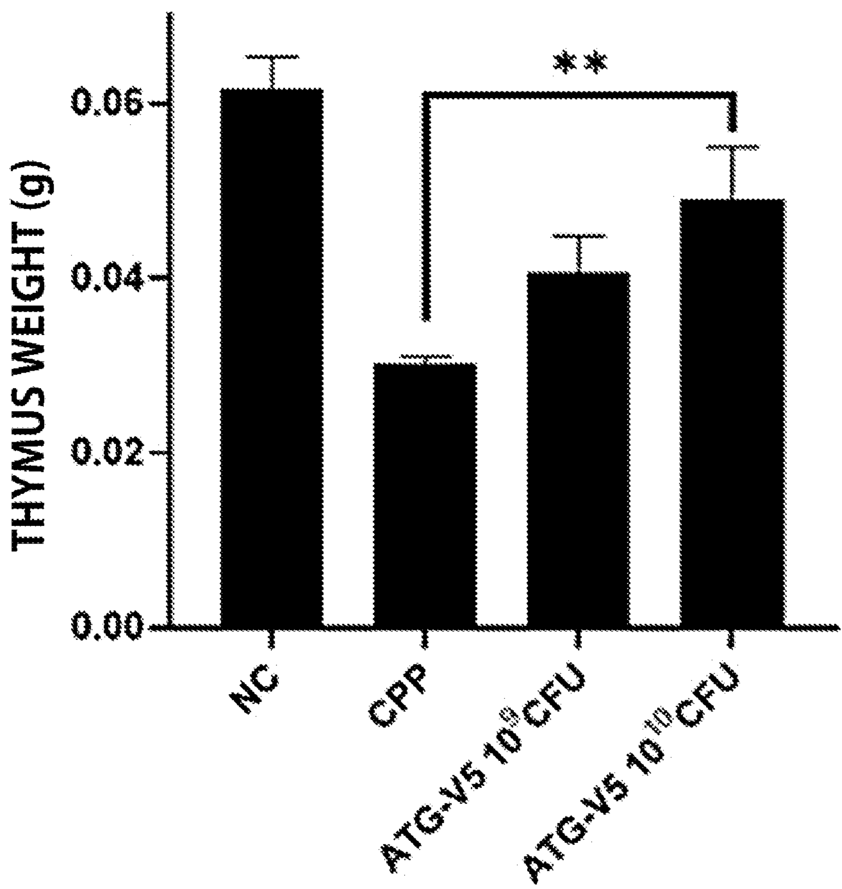
FIG. 11A is a graph showing results of confirming weight changes in the thymus of a CPP-induced animal model by V5 strain administration.
Figure 11B:
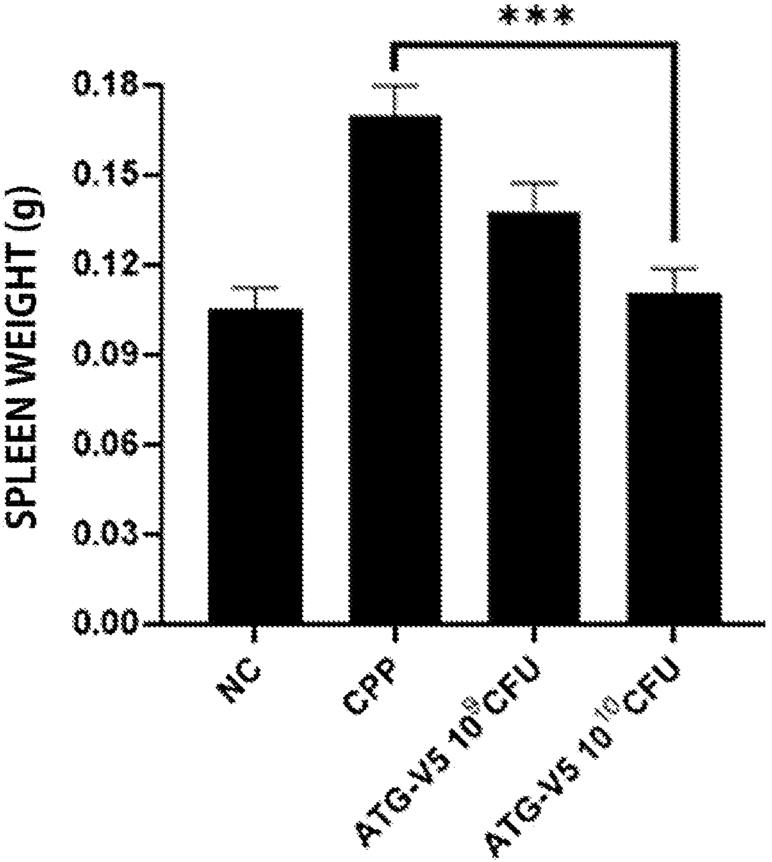
FIG. 11B is a graph showing results of confirming weight changes in the spleen of a CPP-induced animal model by V5 strain administration.

CPP reduced the thymus weight from 0.061 g to 0.03 g and increased the spleen weight from 0.105 g to 0.170 g. In addition, as a result of administering the V5 strain to the CPP-induced animal model, it was confirmed that the thymus weight significantly decreased from 0.031 g (CPP) to 0.048 g (V5 $10^{10}$ CFU), and the spleen weight significantly increased from 0.170 g (CPP) to 0.111 g (V5 $10^{10}$ CFU) (FIGS. 11A and 11B).

<4-3> Confirmation of Enhanced Cytotoxicity of NK Cells in CPP-Induced Animal Model by V5 Strain Administration To measure the cytotoxicity of natural killer cells (NK cells), the spleen was isolated from a CPP-induced animal model, and then the tissue was ground to obtain splenocytes. Next, the splenocytes were mixed with YAC-1 cells in a ratio of the YAC-1 cells: the splenocytes of 1:50 and then incubated in a $CO_2$ incubator at 37° C. for four hours. The amount of LDH was measured using an LDH-cell cytotoxicity assay kit.

Figure 12:
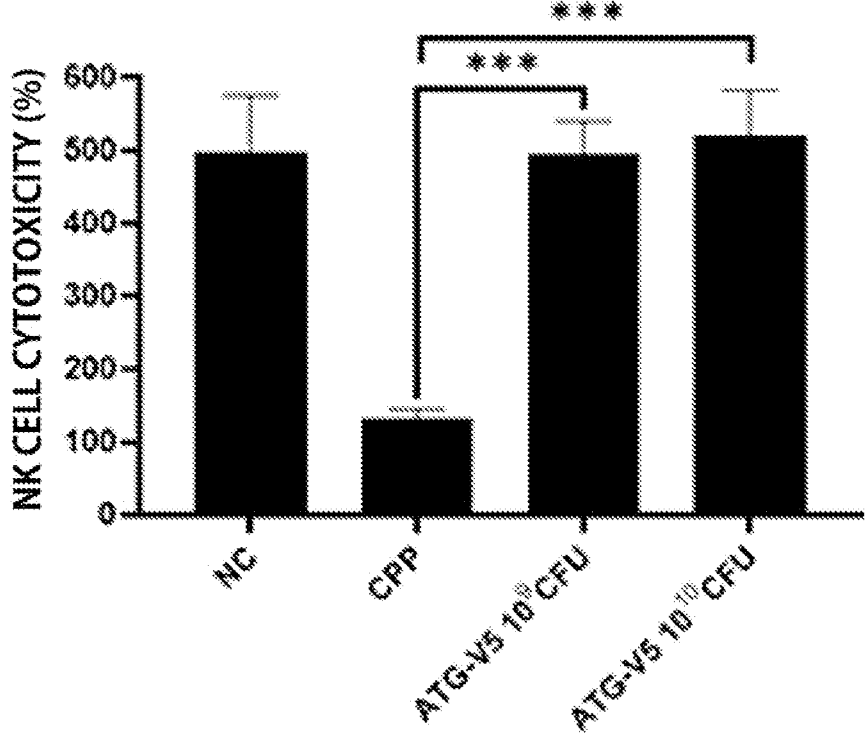
FIG. 12 is a graph showing results of measuring cytotoxicities of natural killer cells (NK cells) in a CPP-induced animal model by V5 strain administration.

As a result, it was confirmed that the V5 strain enhanced the cytotoxicity of the NK cells from 144% (CPP) to 494% (V5 $10^9$ CFU) and 521% (V5 $10^{10}$ CF-U) in the CPP-induced animal model (FIG. 12).

<4-4> Confirmation of Enhanced Cell Viability of Splenocytes in CPP-Induced Animal Model by V5 Strain Administration To measure the cell viability of splenocytes, a collection of cells involved in various cellular immunity, splenocytes from each mouse were seeded in a 96-well plate at $1\times10^4$ cells/well and then incubated in a 37° C. $CO_2$ incubator for 48 hours. Next, the splenocytes were treated with WST to measure cell viability.

Figure 13:
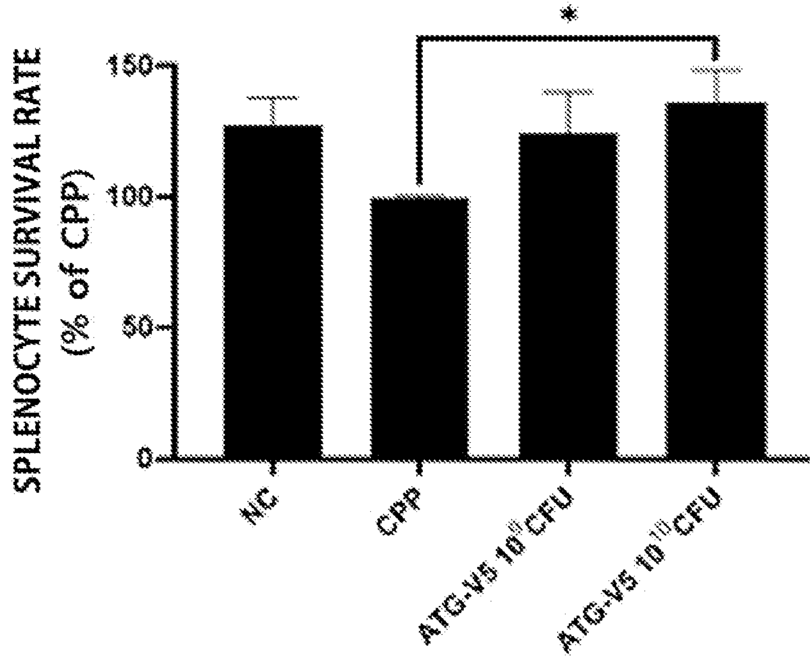
FIG. 13 is a graph showing results of confirming cell viabilities of splenocytes in a CPP-induced animal model by V5 strain administration.
Figure 14A:
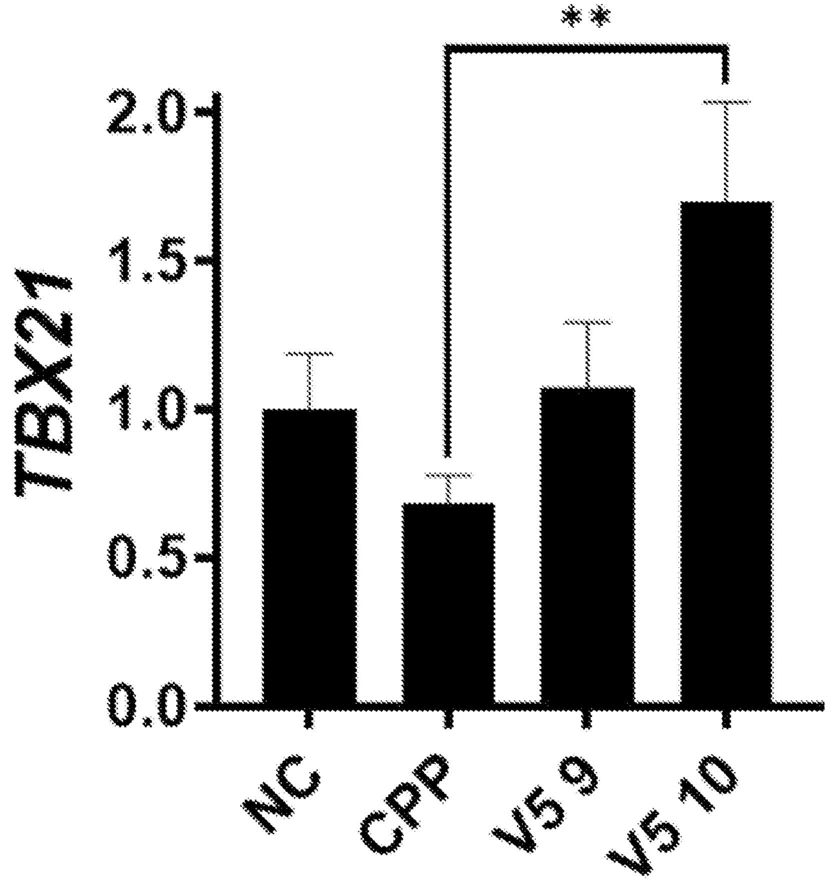
FIG. 14A is a graph showing results of measuring expression levels of T-box transcription factor 21 (TBX21) mRNA in splenocytes of a CPP-induced animal model by V5 strain administration to identify changes in the differentiation of Th1 cells, a T cell subset.
Figure 14B:
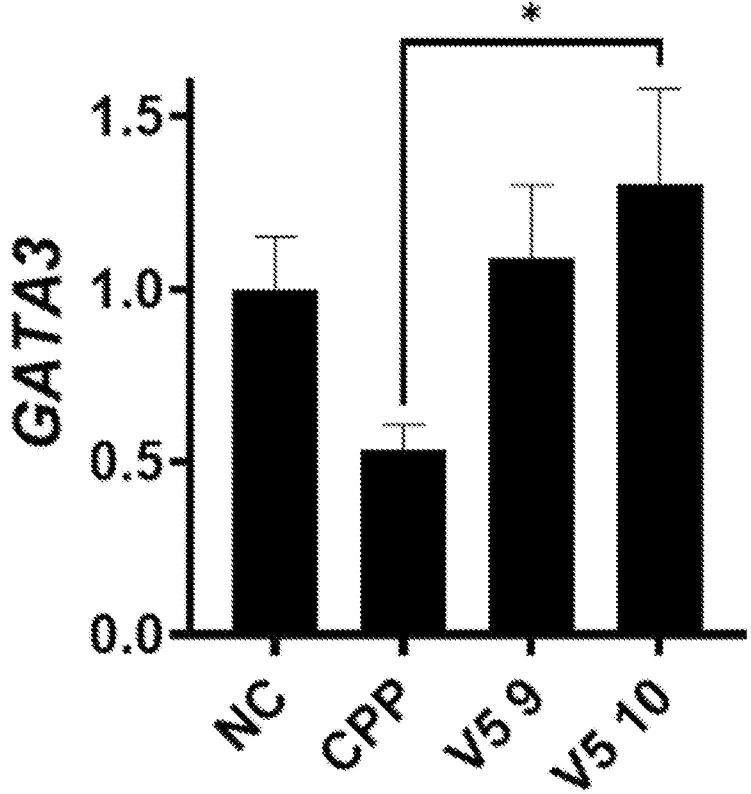
FIG. 14B is a graph showing results of measuring expression levels of GATA binding protein 3 (GATA3) mRNA in splenocytes of a CPP-induced animal model by V5 strain administration to identify changes in the differentiation of Th2 cells, a T cell subset.
Figure 14C:
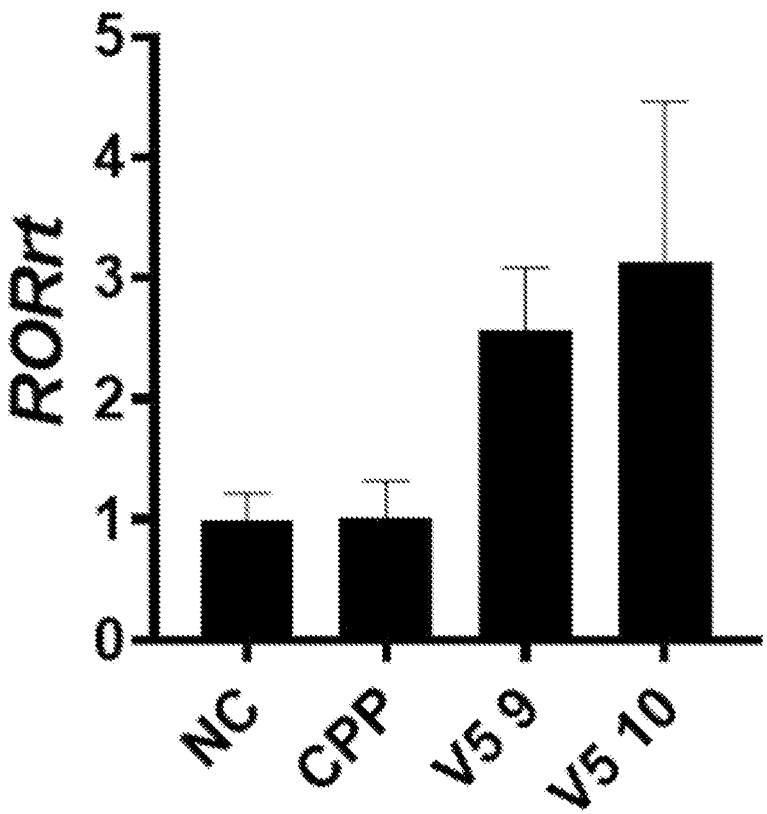
FIG. 14C is a graph showing results of measuring expression levels of ROR-related orphan receptor gamma (RORγt) mRNA in splenocytes of a CPP-induced animal model by V5 strain administration to identify changes in the differentiation of Th17 cells, a T cell subset.
Figure 14D:
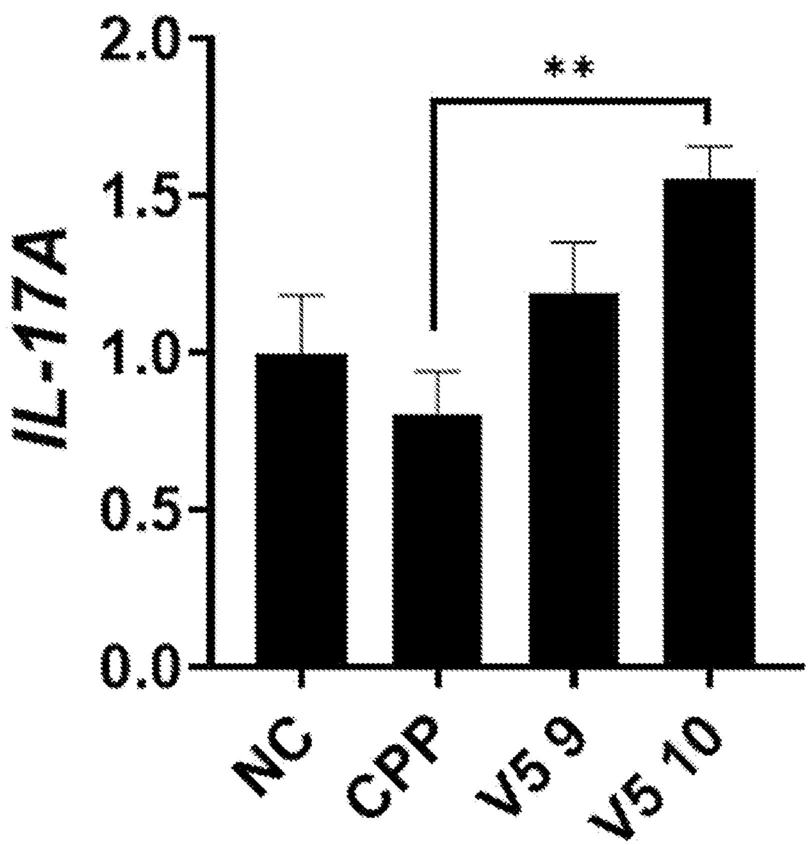
FIG. 14D is a graph showing results of measuring expression levels of interleukin 17 (IL-17) mRNA in splenocytes of a CPP-induced animal model by V5 strain administration to identify changes in the differentiation of Th17 cells, a T cell subset.
Figure 14F:
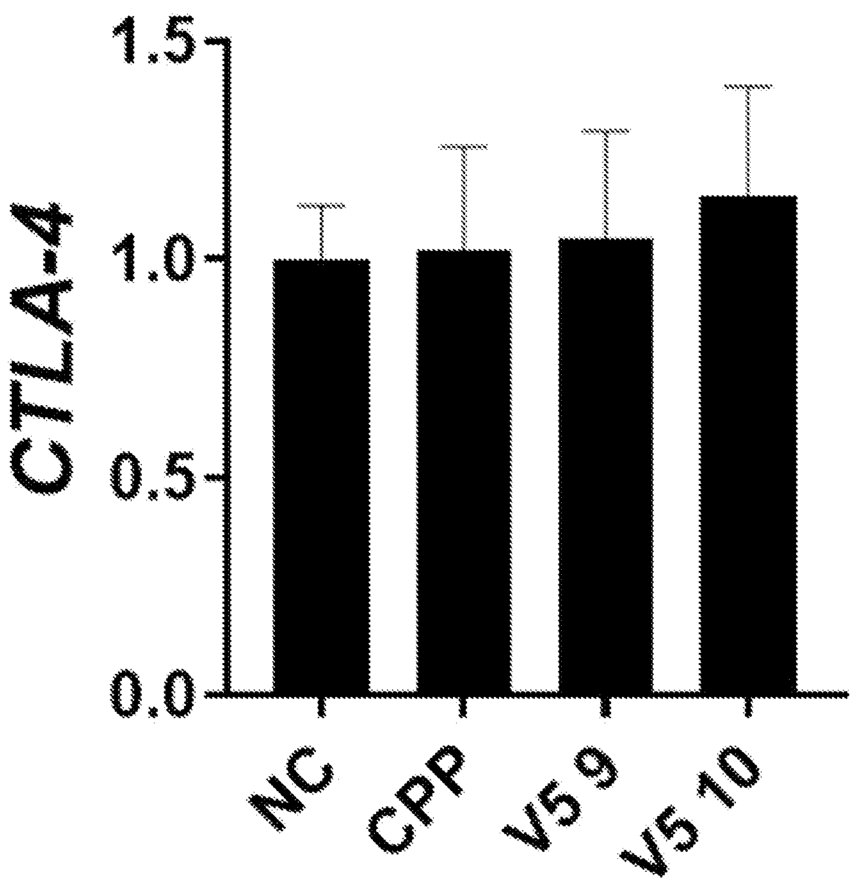
FIG. 14F is a graph showing results of measuring expression levels of cytotoxic T-lymphocyte-associated protein 4 (CTLA-4) mRNA in splenocytes of a CPP-induced animal model by V5 strain administration to identify changes in the differentiation of Treg cells, a T cell subset.

As a result, it was confirmed that the V5 strain enhanced the cell viability of the splenocytes from 99.98% (CPP) to 135.95% (V5 $10^{10}$ CFU) in the CPP-induced animal model (FIG. 13).

<4-5> Confirmation of Changes in T Cell Subsets in Spleen of CPP-Induced Animal Model by V5 Strain Administration In addition, RNA was isolated from the splenocytes at $2\times10^6$ cells/sample using a TRIZOL® reagent (Thermo, US), and cDNA was synthesized using ACCUPOWER® RT PreMix & Master Mix (Bioneer, KO). To confirm changes in differentiation of Th1, Th2, Th17, and Treg cells, T cell subsets, using the synthesized cDNA and ACCUPOWER® GreenStar™ qPCR PreMix (Bioneer, KO), expression levels of TBX21, GATA3, RORγt, IL-17A, Foxp3, and CTLA-4 mRNA in these cells were measured.

As a result, it was confirmed that CPP suppressed the differentiation of naive T cells, thereby suppressing the overall number of T cell subsets, and the V5 strain significantly increased each number of Th1, Th2, Th17, and Treg cells (FIGS. 14A to 14F).

<4-6> Confirmation of Changes in Secretion Amount of Antibodies in Blood of CPP-Induced Animal Model by V5 Strain Administration The blood of a CPP-induced animal model was reacted at room temperature for two hours and then centrifuged at 4000 rpm for 10 minutes to isolate serum. The secretion amounts of IgG, IgA, and IgM were measured from the isolated serum using an ELISA kit (Thermo, US).

Figure 15C:
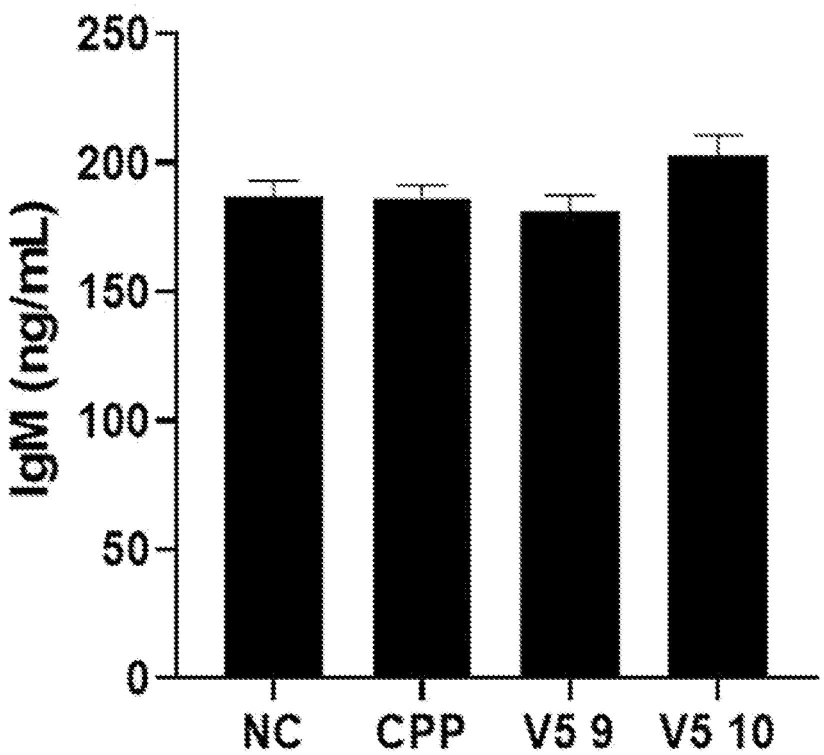
FIG. 15C is a graph showing results of confirming changes in a secretion amount of IgM in the blood of a CPP-induced animal model by V5 strain administration.
Figure 16A:
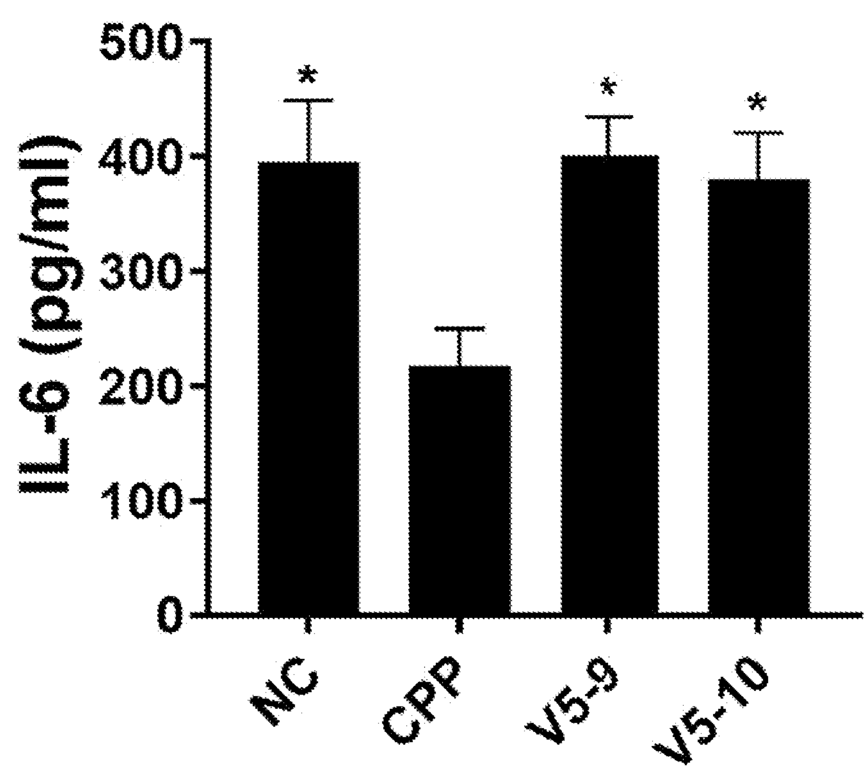
FIG. 16A is a graph showing results of confirming changes in a secretion amount of interleukin 6 (IL-6) in the blood of a CPP-induced animal model by V5 strain administration.
Figure 16B:
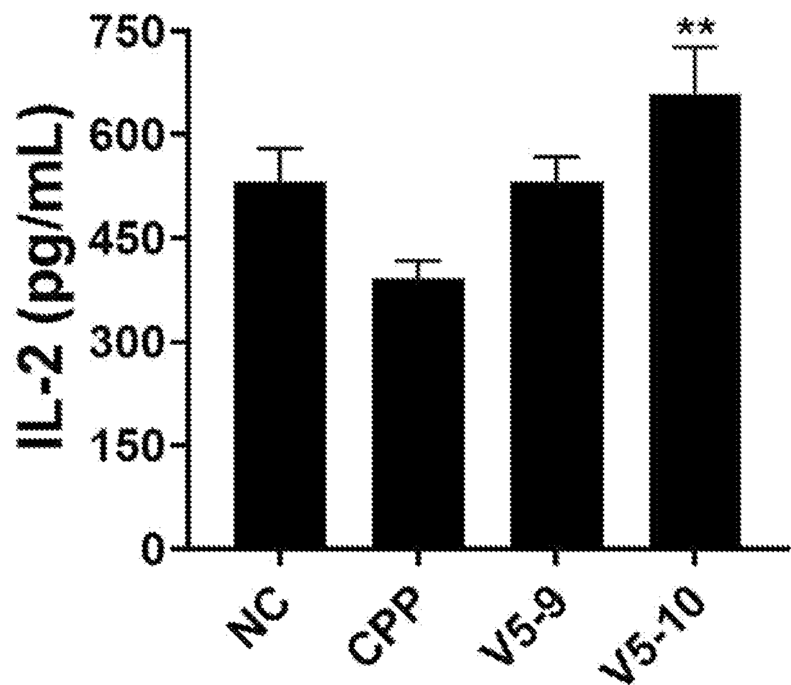
FIG. 16B is a graph showing results of confirming changes in a secretion amount of interleukin 2 (IL-2) in the blood of a CPP-induced animal model by V5 strain administration.
Figure 16C:
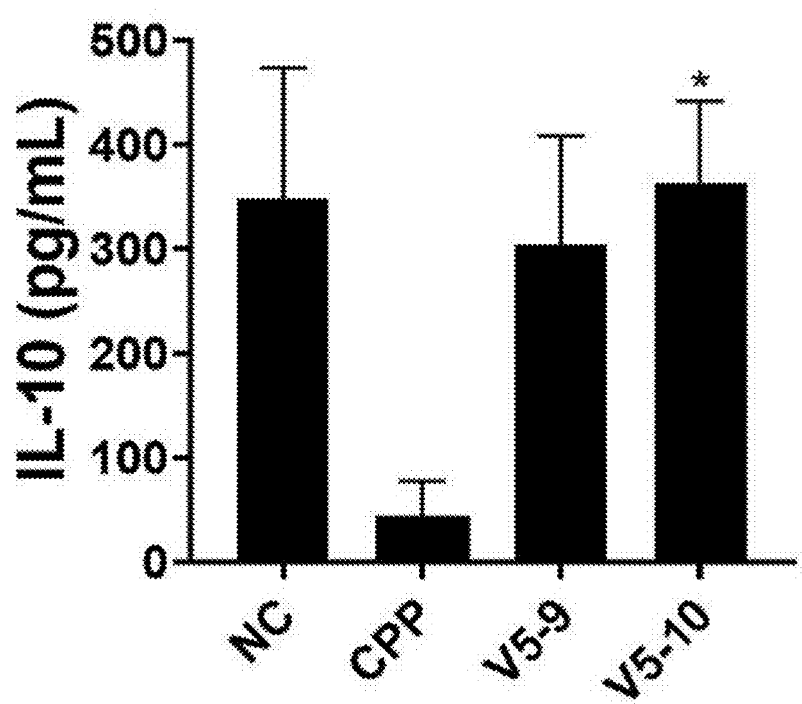
FIG. 16C is a graph showing results of confirming changes in a secretion amount of interleukin 10 (IL-10) in the blood of a CPP-induced animal model by V5 strain administration.
Figure 16D:
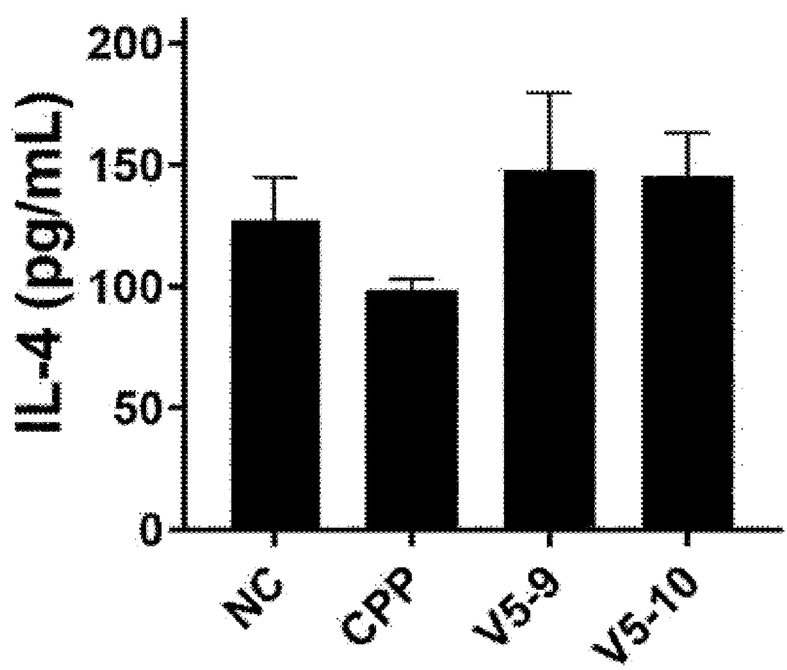
FIG. 16D is a graph showing results of confirming changes in a secretion amount of interleukin 4 (IL-4) in the blood of a CPP-induced animal model by V5 strain administration.

As a result of analyzing the secretion amounts of IgG, IgA, and IgM in the blood of the CPP-induced animal model, it was confirmed that CPP reduced the secretion amounts of IgG and IgA, and the V5 strain increased the secretion amounts of IgG and IgA (FIGS. 15A and 15B). On the other hand, it was confirmed that CPP failed to cause changes in IgM, and the V5 strain also failed to cause changes in IgM (FIG. 15C).

<4-7> Confirmation of Increase in Secretion Amount of Cytokines in Blood of CPP-Induced Animal Model by V5 Strain Administration In addition, enzyme-linked immunosorbent assay (ELISA) for IL-6, IL-2, IL-10, and IL-4 was performed using the serum.

As a result of analyzing the cytokines in the CPP-induced animal model, it was confirmed that there was a tendency in which CPP reduced the overall cytokines, and the V5 strain increased the cytokines (FIGS. 16A to 16D).

DEPOSITARY AUTHORITY

Name of Depositary Authority: Korean Collection for Type Cultures

Accession number: KCTC14481BP

Accession date: 20210304

The invention claimed is:

1. A method for enhancing immunity, the method comprising administering *Lactobacillus fermentum* ATG-V5 strain deposited under accession number KCTC14481BP to a subject in need thereof, wherein the subject is in need of enhanced cytotoxicity of natural killer (NK) cells.

2. The method of claim 1, wherein the strain has the 16S rRNA base sequence of SEQ ID NO: 1.

3. The method of claim 1, wherein the strain increases a secretion amount of nitric oxide (NO) in macrophages.

4. The method of claim 1, wherein the strain enhances phagocytosis of macrophages.

5. The method of claim 1, wherein the strain enhances cell viability of splenocytes.

6. The method of claim 1, wherein the strain increases the number of one or more T cell subsets selected from the group consisting of Th1, Th2, Th17, and Treg cells.

7. The method of claim 1, wherein the strain increases secretion amounts of one or more antibodies selected from the group consisting of IgG and IgA in blood.

8. The method of claim 1, wherein the strain increases secretion amounts of one or more cytokines selected from the group consisting of interleukin 6 (IL-6), interleukin 2 (IL-2), interleukin 10 (IL-10), and interleukin 4 (IL-4) in blood.

9. The method of claim 1, wherein one or more selected from the group consisting of culture media, metabolites, and dead cells of the ATG-V5 strain is further administered to the subject.

* * * * *